(12) United States Patent
Hariton et al.

(10) Patent No.: US 11,337,802 B2
(45) Date of Patent: May 24, 2022

(54) HEART VALVE DELIVERY SYSTEMS AND METHODS

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 115 days.

(21) Appl. No.: 16/135,447

(22) Filed: Sep. 19, 2018

(65) Prior Publication Data

US 2019/0083262 A1    Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2427* (2013.01); *A61F 2/243* (2013.01); *A61F 2/2436* (2013.01);
(Continued)

(58) Field of Classification Search
CPC .. A61F 2/2427–2439; A61F 2/95–9517; A61F 2002/9528–9665;
(Continued)

(56) References Cited

U.S. PATENT DOCUMENTS

| 3,874,388 A | 4/1975 | King et al. |
| 4,222,126 A | 9/1980 | Boretos et al. |

(Continued)

FOREIGN PATENT DOCUMENTS

| CA | 2822801 A1 | 8/2006 |
| CN | 103974674 A | 8/2014 |

(Continued)

OTHER PUBLICATIONS

International Search Report dated Dec. 5, 2011, by the United States Patent and Trademark Office in PCT/IL2011/000582 (3 pages).

(Continued)

*Primary Examiner* — Tan-Uyen T Ho
*Assistant Examiner* — Charles M Wei
(74) *Attorney, Agent, or Firm* — Sughrue Mion, PLLC

(57) ABSTRACT

A heart valve delivery system may be provided. The heart valve delivery system may include at least a first catheter movable relative to second and third catheters, arranged in a telescoping configuration. The second catheter may be movable relative to and extend from the distal end of the third catheter. The delivery system may include a first adjustable flexure radius associated with the second catheter, and a second flexure radius. The delivery system may include at one control handle assembly configured to permit the catheters to rotate together, independently adjust the first and second flexure radii, cause relative axial movement between the catheters, and permit the ejector to cause relative movement between a heart valve and a capsule connected to the first catheter.

21 Claims, 21 Drawing Sheets

(52) U.S. Cl.
CPC .......... *A61F 2/2445* (2013.01); *A61F 2/2454* (2013.01); *A61F 2/2463* (2013.01); *A61F 2/246* (2013.01); *A61F 2/2409* (2013.01); *A61F 2/2418* (2013.01); *A61F 2/2466* (2013.01); *A61F 2210/0014* (2013.01); *A61F 2220/0008* (2013.01); *A61F 2250/007* (2013.01)

(58) Field of Classification Search
CPC .. A61M 2025/1031; A61M 2025/1072; A61M 2025/0175; A61M 2025/0004
See application file for complete search history.

(56) References Cited

U.S. PATENT DOCUMENTS

| | | |
|---|---|---|
| 4,340,091 A | 7/1982 | Skelton et al. |
| 4,972,494 A | 11/1990 | White et al. |
| 5,089,006 A * | 2/1992 | Stiles .................. A61F 2/95 606/198 |
| 5,201,757 A * | 4/1993 | Heyn .................. A61F 2/97 606/198 |
| 5,713,948 A | 2/1998 | Uflacker |
| 5,716,417 A | 2/1998 | Girard et al. |
| 5,741,297 A | 4/1998 | Simon |
| 5,749,920 A * | 5/1998 | Quiachon ............... A61F 2/958 623/1.23 |
| 5,766,151 A * | 6/1998 | Valley ................ A61M 39/0247 604/103.07 |
| 5,776,140 A | 7/1998 | Cottone |
| 5,906,619 A * | 5/1999 | Olson .................. A61F 2/95 606/108 |
| 5,957,949 A | 9/1999 | Leonhardt et al. |
| 5,961,549 A | 10/1999 | Nguyen et al. |
| 6,010,530 A | 1/2000 | Goicoechea |
| 6,083,198 A * | 7/2000 | Afzal .................. A61M 25/007 604/101.01 |
| 6,126,686 A | 10/2000 | Badylak et al. |
| 6,165,183 A | 12/2000 | Kuehn et al. |
| 6,254,609 B1 | 7/2001 | Vrba et al. |
| 6,312,465 B1 | 11/2001 | Griffin et al. |
| 6,346,074 B1 | 2/2002 | Roth |
| 6,402,780 B2 | 6/2002 | Williamson, IV et al. |
| 6,458,153 B1 | 10/2002 | Bailey et al. |
| 6,669,724 B2 | 12/2003 | Park et al. |
| 6,733,525 B2 | 5/2004 | Yang et al. |
| 6,752,813 B2 | 6/2004 | Goldfarb et al. |
| 6,755,857 B2 | 6/2004 | Peterson et al. |
| 6,849,084 B2 * | 2/2005 | Rabkin .................. A61F 2/966 623/1.12 |
| 6,926,715 B1 | 8/2005 | Hauck et al. |
| 6,939,370 B2 * | 9/2005 | Hartley .................. A61F 2/95 623/1.11 |
| 7,074,236 B2 | 7/2006 | Rabkin et al. |
| 7,201,772 B2 | 4/2007 | Schwammenthal et al. |
| 7,226,467 B2 | 6/2007 | Lucatero et al. |
| 7,261,686 B2 | 8/2007 | Couvillon, Jr. |
| 7,288,097 B2 | 10/2007 | Séguin |
| 7,442,204 B2 | 10/2008 | Schwammenthal et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,736,388 B2 | 6/2010 | Goldfarb et al. |
| 7,753,949 B2 | 7/2010 | Lamphere et al. |
| 7,811,296 B2 | 10/2010 | Goldfarb et al. |
| 7,837,727 B2 | 11/2010 | Goetz et al. |
| 7,959,672 B2 | 6/2011 | Salahieh et al. |
| 7,993,392 B2 * | 8/2011 | Righini ................ A61F 2/2436 623/2.11 |
| 8,052,592 B2 | 11/2011 | Goldfarb et al. |
| 8,057,493 B2 | 11/2011 | Goldfarb et al. |
| 8,070,802 B2 | 12/2011 | Lamphere et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,216,256 B2 | 7/2012 | Raschdorf, Jr. et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,585,755 B2 | 11/2013 | Chau et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Gross et al. |
| 8,998,982 B2 | 4/2015 | Richter et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,060,858 B2 | 6/2015 | Thornton et al. |
| 9,072,603 B2 | 7/2015 | Tuval et al. |
| 9,095,434 B2 | 8/2015 | Rowe |
| 9,119,719 B2 | 9/2015 | Zipory et al. |
| 9,125,740 B2 | 9/2015 | Morriss et al. |
| 9,132,009 B2 | 9/2015 | Hacohen et al. |
| 9,173,659 B2 | 11/2015 | Bodewadt et al. |
| 9,180,009 B2 | 11/2015 | Majkrzak et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,277,994 B2 | 3/2016 | Miller et al. |
| 9,295,551 B2 | 3/2016 | Straubinger et al. |
| 9,295,552 B2 | 3/2016 | McLean et al. |
| 9,320,591 B2 | 4/2016 | Bolduc |
| D755,384 S | 5/2016 | Pesce et al. |
| 9,345,573 B2 | 5/2016 | Nyuli et al. |
| 9,358,107 B2 | 6/2016 | Nguyen et al. |
| 9,387,078 B2 | 7/2016 | Gross et al. |
| 9,393,110 B2 | 7/2016 | Levi et al. |
| 9,439,757 B2 | 9/2016 | Wallace et al. |
| 9,445,893 B2 | 9/2016 | Vaturi |
| 9,463,102 B2 | 10/2016 | Kelly |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 10,010,414 B2 | 7/2018 | Cooper et al. |
| 10,076,415 B1 | 9/2018 | Metchik et al. |

(56) References Cited

U.S. PATENT DOCUMENTS

| | | |
|---|---|---|
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,357,360 B2 | 7/2019 | Hariton et al. |
| 10,376,361 B2 | 8/2019 | Gross et al. |
| 10,390,952 B2 | 8/2019 | Hariton et al. |
| 10,426,610 B2 | 10/2019 | Hariton et al. |
| 10,463,487 B2 | 11/2019 | Hariton et al. |
| 10,463,488 B2 | 11/2019 | Hariton et al. |
| 10,492,907 B2 * | 12/2019 | Duffy ................ A61F 2/2433 |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,631,984 B2 * | 4/2020 | Nyuli ................ A61F 2/2436 |
| 10,646,342 B1 | 5/2020 | Marr et al. |
| 10,667,908 B2 | 6/2020 | Hariton et al. |
| 10,682,227 B2 | 6/2020 | Hariton et al. |
| 10,695,177 B2 | 6/2020 | Hariton et al. |
| 10,702,385 B2 | 7/2020 | Hacohen |
| 10,722,360 B2 | 7/2020 | Hariton et al. |
| 10,758,342 B2 | 9/2020 | Chau et al. |
| 10,758,344 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 | 1/2021 | Hariton et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,483 B2 | 2/2021 | Metchik et al. |
| 10,925,595 B2 | 2/2021 | Hacohen et al. |
| 10,945,844 B2 | 3/2021 | McCann et al. |
| 10,973,636 B2 | 4/2021 | Hariton et al. |
| 10,993,809 B2 | 5/2021 | McCann et al. |
| 11,083,582 B2 | 8/2021 | McCann et al. |
| 11,147,672 B2 | 10/2021 | McCann et al. |
| 2001/0005787 A1 | 6/2001 | Oz et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2003/0050694 A1 | 3/2003 | Yang et al. |
| 2003/0074059 A1 | 4/2003 | Nguyen et al. |
| 2004/0030382 A1 | 2/2004 | St. Goar et al. |
| 2004/0186558 A1 | 9/2004 | Pavcnik et al. |
| 2004/0210304 A1 | 10/2004 | Seguin et al. |
| 2004/0236354 A1 | 11/2004 | Seguin |
| 2004/0249433 A1 | 12/2004 | Freitag |
| 2005/0027348 A1 | 2/2005 | Case et al. |
| 2005/0080474 A1 | 4/2005 | Andreas et al. |
| 2005/0085900 A1 | 4/2005 | Case et al. |
| 2005/0137681 A1 | 6/2005 | Shoemaker et al. |
| 2005/0137691 A1 | 6/2005 | Salahieh et al. |
| 2005/0137692 A1 | 6/2005 | Haug et al. |
| 2005/0137697 A1 | 6/2005 | Salahieh et al. |
| 2005/0203618 A1 | 9/2005 | Sharkawy et al. |
| 2005/0240200 A1 | 10/2005 | Bergheim |
| 2005/0256566 A1 | 11/2005 | Gabbay |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0030863 A1 * | 2/2006 | Fields ............. A61B 17/12104 606/108 |
| 2006/0052867 A1 | 3/2006 | Revuelta et al. |
| 2006/0184203 A1 | 8/2006 | Martin et al. |
| 2006/0195183 A1 | 8/2006 | Navia et al. |
| 2006/0216404 A1 | 9/2006 | Seyler et al. |
| 2006/0229708 A1 | 10/2006 | Powell et al. |
| 2006/0259137 A1 | 11/2006 | Artof et al. |
| 2006/0282150 A1 | 12/2006 | Olson et al. |
| 2007/0016286 A1 | 1/2007 | Herrmann et al. |
| 2007/0038293 A1 | 2/2007 | St. Goar et al. |
| 2007/0056346 A1 | 3/2007 | Spenser et al. |
| 2007/0078510 A1 | 4/2007 | Ryan |
| 2007/0197858 A1 | 8/2007 | Goldfarb et al. |
| 2007/0198077 A1 | 8/2007 | Cully et al. |
| 2007/0021381 A1 | 9/2007 | Newhauser et al. |
| 2007/0213810 A1 | 9/2007 | Newhauser et al. |
| 2007/0219630 A1 | 9/2007 | Chu |
| 2007/0239273 A1 | 10/2007 | Allen |
| 2007/0244546 A1 | 10/2007 | Francis |
| 2008/0065011 A1 | 3/2008 | Marchand et al. |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2009/0005863 A1 | 1/2009 | Goetz et al. |
| 2009/0105794 A1 * | 4/2009 | Ziarno ................ A61F 2/2433 607/120 |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0022823 A1 | 1/2010 | Goldfarb et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keränen et al. |
| 2011/0004227 A1 | 1/2011 | Goldfarb et al. |
| 2011/0004299 A1 | 1/2011 | Navia et al. |
| 2011/0029072 A1 | 2/2011 | Gabbay |
| 2011/0066233 A1 | 3/2011 | Thornton et al. |
| 2011/0098805 A1 * | 4/2011 | Dwork ................ A61F 2/2436 623/2.11 |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |

(56) References Cited

U.S. PATENT DOCUMENTS

| | | |
|---|---|---|
| 2011/0282439 A1 | 11/2011 | Thill et al. |
| 2011/0306916 A1 | 12/2011 | Nitzan et al. |
| 2011/0307049 A1 | 12/2011 | Kao |
| 2011/0313515 A1 | 12/2011 | Quadri et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0089223 A1 | 4/2012 | Nguyen et al. |
| 2012/0101571 A1 | 4/2012 | Thambar et al. |
| 2012/0165930 A1 | 6/2012 | Gifford, III et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0066342 A1 | 3/2013 | Dell et al. |
| 2013/0144381 A1 | 6/2013 | Quadri et al. |
| 2013/0178930 A1 | 7/2013 | Straubinger et al. |
| 2013/0190861 A1 | 7/2013 | Chau et al. |
| 2013/0231735 A1* | 9/2013 | Deem .................. A61F 2/243 623/2.11 |
| 2013/0253643 A1 | 9/2013 | Rolando et al. |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289740 A1 | 10/2013 | Liddy et al. |
| 2013/0304200 A1 | 11/2013 | McLean et al. |
| 2014/0000112 A1 | 1/2014 | Braido et al. |
| 2014/0018915 A1 | 1/2014 | Biadillah et al. |
| 2014/0067050 A1* | 3/2014 | Costello .................. A61F 2/966 623/2.11 |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2015/0018944 A1 | 1/2015 | O'Connell et al. |
| 2015/0032205 A1 | 1/2015 | Matheny |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0238315 A1* | 8/2015 | Rabito .................. A61F 2/2436 623/2.11 |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0100939 A1 | 4/2016 | Amstrong et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0158497 A1* | 6/2016 | Tran .................. A61F 2/2436 623/2.11 |
| 2016/0175095 A1 | 6/2016 | Dienno et al. |
| 2016/0184098 A1 | 6/2016 | Vaturi |
| 2016/0262885 A1* | 9/2016 | Sandstrom ............ A61F 2/2436 |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0338706 A1 | 11/2016 | Rowe |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056169 A1* | 3/2017 | Johnson .................. A61F 2/2436 |
| 2017/0056171 A1 | 3/2017 | Cooper et al. |
| 2017/0065411 A1 | 3/2017 | Grundeman et al. |
| 2017/0128205 A1 | 5/2017 | Tamir et al. |
| 2017/0135816 A1 | 5/2017 | Lashinski et al. |
| 2017/0143938 A1* | 5/2017 | Ogle .................. A61M 1/008 |
| 2017/0189174 A1 | 7/2017 | Braido et al. |
| 2017/0209264 A1 | 7/2017 | Chau et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231766 A1 | 8/2017 | Hariton et al. |
| 2017/0239048 A1 | 8/2017 | Goldfarb et al. |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0367823 A1 | 12/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055630 A1 | 3/2018 | Patel et al. |
| 2018/0098850 A1 | 4/2018 | Rafiee et al. |
| 2018/0116843 A1 | 5/2018 | Schreck et al. |
| 2018/0125644 A1 | 5/2018 | Conklin |
| 2018/0153689 A1 | 6/2018 | Maimon et al. |
| 2018/0206983 A1 | 7/2018 | Noe et al. |
| 2018/0214263 A1 | 8/2018 | Rolando et al. |
| 2018/0250126 A1 | 9/2018 | O'Connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |

(56) References Cited

U.S. PATENT DOCUMENTS

| | | |
|---|---|---|
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0192295 A1 | 6/2019 | Spence et al. |
| 2019/0328519 A1 | 10/2019 | Hariton et al. |
| 2019/0336280 A1 | 11/2019 | Naor et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |
| 2020/0163761 A1 | 5/2020 | Hariton et al. |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |
| 2021/0085455 A1 | 3/2021 | Bateman et al. |
| 2021/0093449 A1 | 4/2021 | Hariton et al. |
| 2021/0113331 A1 | 4/2021 | Quadri et al. |

FOREIGN PATENT DOCUMENTS

| | | | |
|---|---|---|---|
| EP | | 1264582 A2 | 12/2002 |
| EP | | 1637092 A2 | 3/2006 |
| EP | | 2349124 B1 | 10/2018 |
| EP | | 3583922 A1 | 12/2019 |
| EP | | 3270825 B1 | 4/2020 |
| EP | | 2485795 B1 | 9/2020 |
| WO | WO 2003/020179 A1 | | 3/2003 |
| WO | WO 2004/028399 A2 | | 4/2004 |
| WO | WO 2006/007389 A1 | | 1/2006 |
| WO | WO 2006/086434 A1 | | 8/2006 |
| WO | WO 2006/116558 A2 | | 11/2006 |
| WO | WO 2006/0128193 A3 | | 11/2006 |
| WO | WO 20047/047488 A2 | | 4/2007 |
| WO | WO 2008/029296 A2 | | 3/2008 |
| WO | WO 2009/091509 A1 | | 7/2009 |
| WO | WO 2010/006627 A1 | | 1/2010 |
| WO | WO 2010/027485 A1 | | 3/2010 |
| WO | WO 2010/045297 A2 | | 4/2010 |
| WO | WO 2010/057262 A1 | | 5/2010 |
| WO | WO 2011/069048 A2 | | 6/2011 |
| WO | WO 2011/144351 A2 | | 11/2011 |
| WO | WO 2012/011108 A2 | | 1/2012 |
| WO | WO 2012/036740 A2 | | 3/2012 |
| WO | WO 2012/048035 A2 | | 4/2012 |
| WO | WO 2013/059747 A1 | | 4/2013 |
| WO | WO 2013/072496 A1 | | 5/2013 |
| WO | WO 2013/078497 A1 | | 6/2013 |
| WO | WO 2013/114214 A2 | | 8/2013 |
| WO | WO 2013/175468 A2 | | 11/2013 |
| WO | WO 2014/115149 A2 | | 7/2014 |
| WO | WO 2014/144937 A2 | | 9/2014 |
| WO | WO 2014/164364 A1 | | 10/2014 |
| WO | WO 2016/016899 A1 | | 2/2016 |
| WO | WO 2016/098104 A2 | | 6/2016 |
| WO | WO 2016/125160 A1 | | 8/2016 |
| WO | WO 2016/150806 A1 | | 9/2016 |
| WO | WO 2018/025260 A1 | | 2/2018 |
| WO | WO 2018/025263 A2 | | 2/2018 |
| WO | WO 2018/029680 A1 | | 2/2018 |
| WO | WO 2018/039631 A1 | | 3/2018 |
| WO | WO 2018/112429 A1 | | 6/2018 |
| WO | WO 2018/118717 A1 | | 6/2018 |
| WO | WO 2018/131042 A1 | | 7/2018 |
| WO | WO 2018/131043 A1 | | 7/2018 |
| WO | WO 2019/027507 A1 | | 2/2019 |
| WO | WO 2019/195860 A2 | | 10/2019 |
| WO | WO 2020/167677 A1 | | 8/2020 |

OTHER PUBLICATIONS

International Search Report dated Mar. 27, 2018, by the European Patent Office in PCT/IL2017/050849 (5 pages).
International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).
Written Opinion of the International Searching Authority issued by the United States Patent and Trademark Office in PCT/IL2011/000582 (12 pages).
Written Opinion of the International Searching Authority issued by the European Patent Office in PCT/IL2017/050849 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).
Written Opinion of the International Searching Authority issued by the European Patent Office in PCT/IL2015/050792 (5 pages).
Written Opinion of the International Searching Authority issued by the European Patent Office in PCT/IL2017/050873 (12 pages).
Sündermann, Simon H. et al., *Feasibility of the Engager™ aortic transcatheter valve system using a flexible over-the-wire design*, 42 European Journal of Cardio-Thoracic Surgery, Jun. 27, 2012, at e48 (5 pages).
Symetis S.A., Clinical Investigation Plan for ACURATE Neo™ TA Delivery System, Protocol Jan. 2015, ver. 2, ClinicalTrials.gov Identifier NCT02950428, Sep. 8, 2015 (76 pages).
Tchetche, Didier et al., *New-generation TAVI devices: description and specifications*, 10 EuroIntervention (Supplement), Sep. 2014, at U90 (11 pages).
*Edwards Lifesciences Corp.* v. *Cardiovalve Ltd.*, IPR2021-00383, Exhibit 1014: Transcript of proceedings held May 20, 2021 (May 26, 2021) (21 pages).
*Edwards Lifesciences Corp.* v. *Cardiovalve Ltd.*, IPR2021-00383, Exhibit 1015: Facilitate, Merriam-Webster.com, https://www. www.merriam-webster.com/dictionary/facilitate (accessed May 27, 2021) (5 pages).
*Edwards Lifesciences Corp.* v. *Cardiovalve Ltd.*, IPR2021-00383, Paper 12: Petitioners' Authorized Reply to Patent Owner's Preliminary Response (May 27, 2021) (9 pages).
*Edwards Lifesciences Corp.* v. *Cardiovalve Ltd.*, IPR2021-00383, Paper 13: Patent Owner's Authorized Surreply to Petitioner's Reply to Patent Owner's Preliminary Response (Jun. 4, 2021) (8 pages).

(56) References Cited

OTHER PUBLICATIONS

*Edwards Lifesciences Corp. v. Cardiovalve Ltd.*, IPR2021-00383, Paper 16: Institution Decision (Jul. 20, 2021) (51 pages).
Batista, Randas J. V. et al., *Partial Left Ventriculectomy to Treat End-Stage Heart Disease*, 64 Annals Thoracic Surgery 634-38 (1997) (5 pages).
Beall, Jr., Arthur C. et al., *Clinical Experience with a Dacron Velour-Covered Teflon-Disc Mitral-Valve Prosthesis*, 5 Annals Thoracic Surgery 402-10 (1968) (9 pages).
Fucci, Carlo et al., *Improved Results with Mitral Valve Repair Using New Surgical Techniques*, 9 Eur. J. Cardiothoracic Surgery 621-27 (1995) (7 pages).
Maisano, Francesco et al., *The Edge-To-Edge Technique: A Simplified Method to Correct Mitral Insufficiency*, 13 Eur. J. Cardiothoracic Surgery 240-46 (1998) (7 pages).
Stone, Gregg W. et al., *Clinical Trial Design Principles and Endpoint Definitions for Transcatheter Mitral Valve Repair and Replacement: Part 1: Clinical Trial Design Principles*, 66 J. Am. C. Cardiology 278-307 (2015) (30 pages).
Poirier, Nancy et al., *A Novel Repair for Patients with Atrioventricular Septal Defect Requiring Reoperation for Left Atrioventricular Valve Regurgitation*, 18 Eur. J. Cardiothoracic Surgery 54-61 (2000) (8 pages).
Ando, Tomo et al., *Iatrogenic Ventricular Septal Defect Following Transcatheter Aortic Valve Replacement: A Systematic Review*, 25 Heart, Lung, and Circulation 968-74 (2016) (7 pages).
Urina, Marina et al., *Transseptal Transcatheter Mitral Valve Replacement Using Balloon-Expandable Transcatheter Heart Valves*, JACC: Cardiovascular Interventions 1905-19 (2017) (15 pages).
Ando, Tomo et al., "Iatrogenic Ventricular Septal Defect Following Transcatheter Aortic Valve Replacement: A Systematic Review," *Heart, Lung, and Circulation* (2016) 25, 968-974, http://dx.doi.org/10.1016/j.hlc.2016.03.012, © 2016, Accepted on Mar. 12, 2016, 7 pgs.
Poirier, Nancy C. et al., "A Novel Repair for Patients with Atrioventricular Septal Defect Requiring Reoperation for Left Atrioventricular Valve Regurgitation," *European Journal of Cardio-thoracic Surgery* 18 (2000) 54-61, Accepted on Feb. 22, 2000, © 2000 Elsevier Science B.V., 8 pgs.
Urena, Marina et al., "Transseptal Transcatheter Mitral Valve Replacement Using Balloon-Expandable Transcatheter Heart Valves," *JACC: Cardiovascular Interventions*, © 2017 by the American College of Cardiology Foundation, pub. by Elsevier, vol. 10, No. 19, Accepted on Jun. 29, 2017, 15 pgs.
*Edwards Lifesciences Corporation and Edwards Lifesciences LLC*, Petitioner v. *Cardiovalve Ltd.*, Patent Owner, Case No. IPR2021-00383, U.S. Pat. No. 10,226,341, Deposition of Dr. Ivan Vesely, Ph D., Washington, D.C., Sep. 22, 2021, reported by Mary Ann Payonk, Job No. 199935, TSG Reporting-Worldwide, Cardiovalve Exhibit 2010, 170 pgs.
Fann, James I., et al., "Beating Heart Catheter-Based Edge-to-Edge Mitral Valve Procedure in a Porcine Model, Efficacy and Hearing Response," *Circulation*, 110:988-993, originally published Aug. 9, 2004, 6 pgs.
Feldman, Ted et al., "Percutaneous Mitral Valve Repair Using the Edge-to-Edge Technique, Six-Month Results of the EVEREST Phase I Clinical Trial," *J Am Coll Cardiol*, 2005; vol. 46, No. 11, 2134-40, available online Oct. 19, 2005, 7 pgs.
Feldman, Ted et al., "Percutaneous Mitral Repair With the MitraClip System, Safety and Midterm Durability in the Initial EVEREST (Endovascular Valve Edge-to-Edge REpair Study) Cohort," *J Am Coll Cardiol*, 2009;54:686-94, available online Aug. 11, 2009, 9 pgs.
Feldman, Ted et al., "Percutaneous Mitral Leaflet Repair: MitraClip® Therapy for Mitral Regurgitation," *Informa Healthcare*, ©2012, ISBN: 13:978-1-84184-966-9, Version Date Jan. 16, 2005, 8 pgs.
Fucci, C. et al., "Improved Results with Mitral Valve Repair Using New Surgical Techniques," *Eur J Cardio-thorac Surg*, © Springer-Verlag 1995, Eur J Cardio-thorac Surg (1995) 9: 621-627, published Nov. 1, 1995, 7 pgs.
Maisano, Francesco et al., "The Evolution From Surgery to Percutaneous Mitral Valve Interventions, The Role of the Edge-to-Edge Technique," *J Am Coll Cardiol*, 2011;58:2174-82, available online Nov. 8, 2011, 9 pgs.
Maisano, F. et al., "The Edge-to-Edge Technique: A Simplified Method to Correct Mitral Insufficiency," *European Journal of Cardio-thoracic Surgery* 13 (1998) 240-246, published Mar. 1, 1998, 7 pgs.
*Edwards Lifesciences Corporation and Edwards Lifesciences LLC*, Petitioners, v. *Cardiovalve Ltd.*, Patent Owner, IPR2021-00383, U.S. Pat. No. 10,226,341, Patent Owner's Response Pursuant to 37 C.F.R. § 42.120, 75 pgs.
*Edwards Lifesciences Corporation and Edwards Lifesciences LLC*, Petitioners, v. *Cardiovalve Ltd.*, Patent Owner, IPR2021-00383, U.S. Pat. No. 10,226,341, Second Declaration of Dr. Michael Sacks, Cardiovalve Exhibit 2014, 28 pgs.
*Edwards Lifesciences Corporation and Edwards Lifesciences LLC*, Petitioners, v. *Cardiovalve Ltd.*, Patent Owner, IPR2021-00383, U.S. Pat. No. 10,226,341, Patent Owner's Contingent Motion to Amend under 37 C.F.R. §42.121, 35 pgs.
*Edwards Lifesciences Corp. v. Cardiovalve Ltd.*, IPR2021-00383, Paper 10: Decision Granting Institution of Inter Partes Review (Dec. 10, 2021) (42 pages).
*Edwards Lifesciences Corp. v. Cardiovalve Ltd.*, IPR2021-00383, Petitioners' Opposition to Patent Owner's Contingent Motion to Amend (Jan. 5, 2022) (32 pages).
*Edwards Lifesciences Corp. v. Cardiovalve Ltd.*, IPR2021-00383, Petitioners' Reply to Patent Owner's Response (Jan. 5, 2022) (41 pages).

* cited by examiner

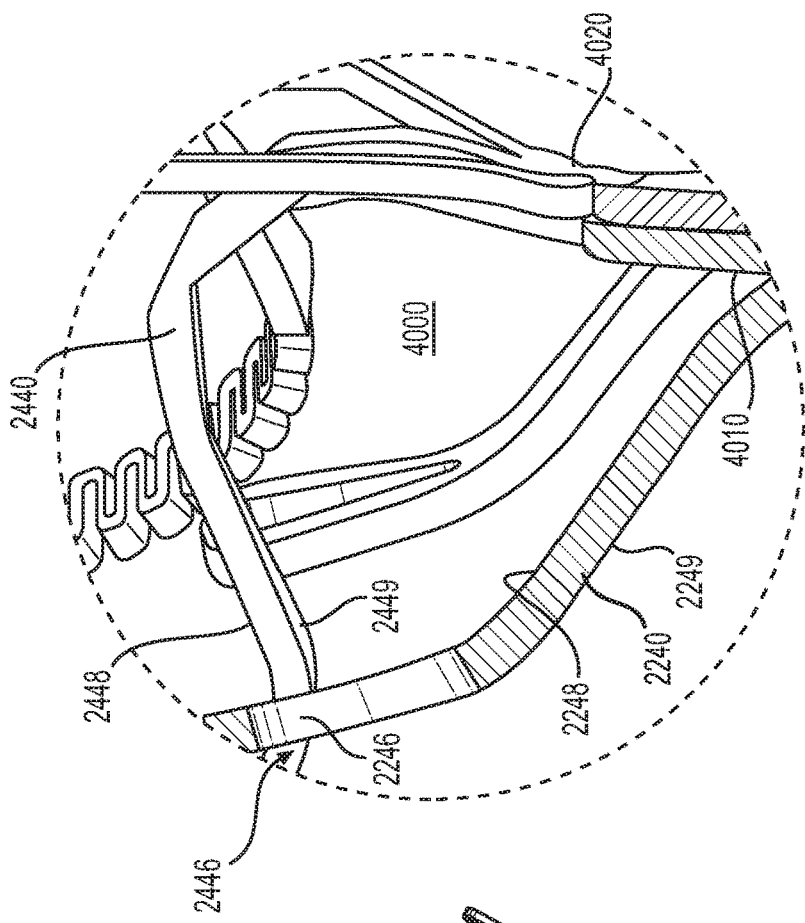
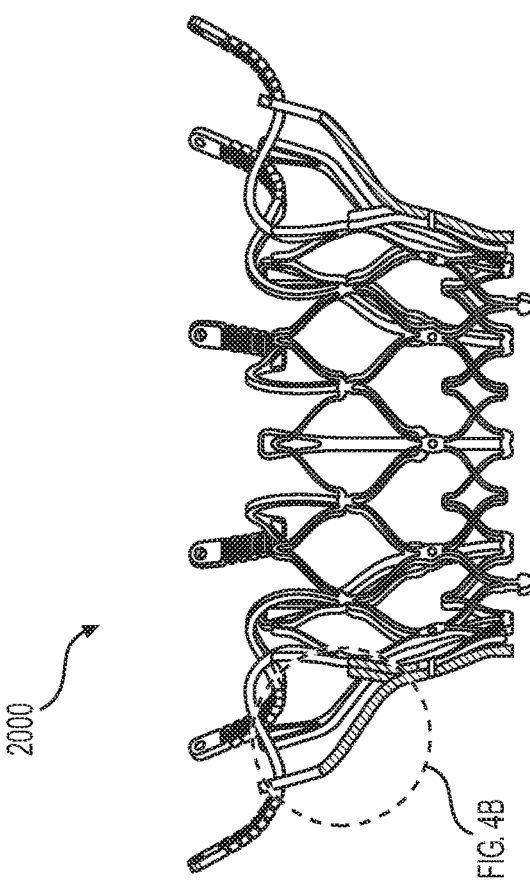
FIG. 4B
FIG. 4A

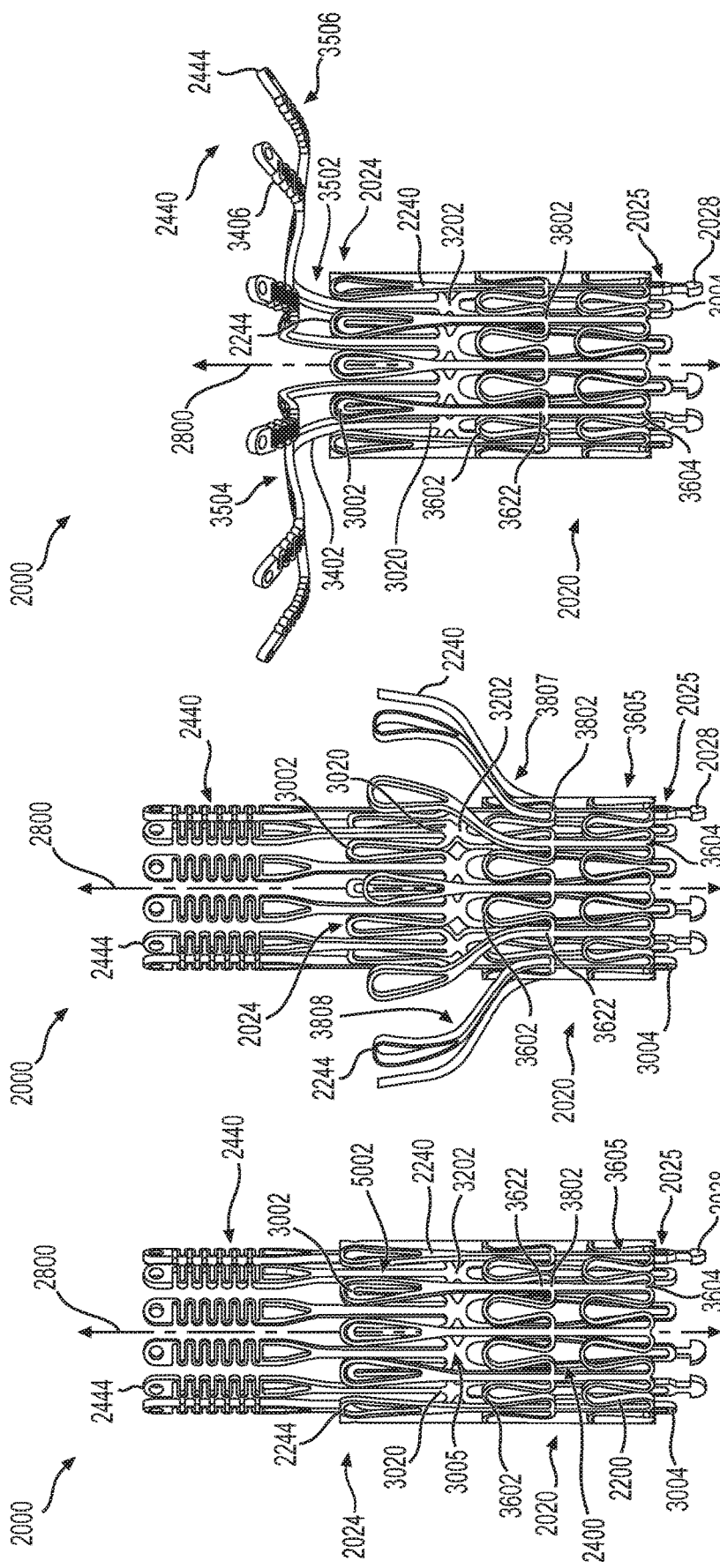

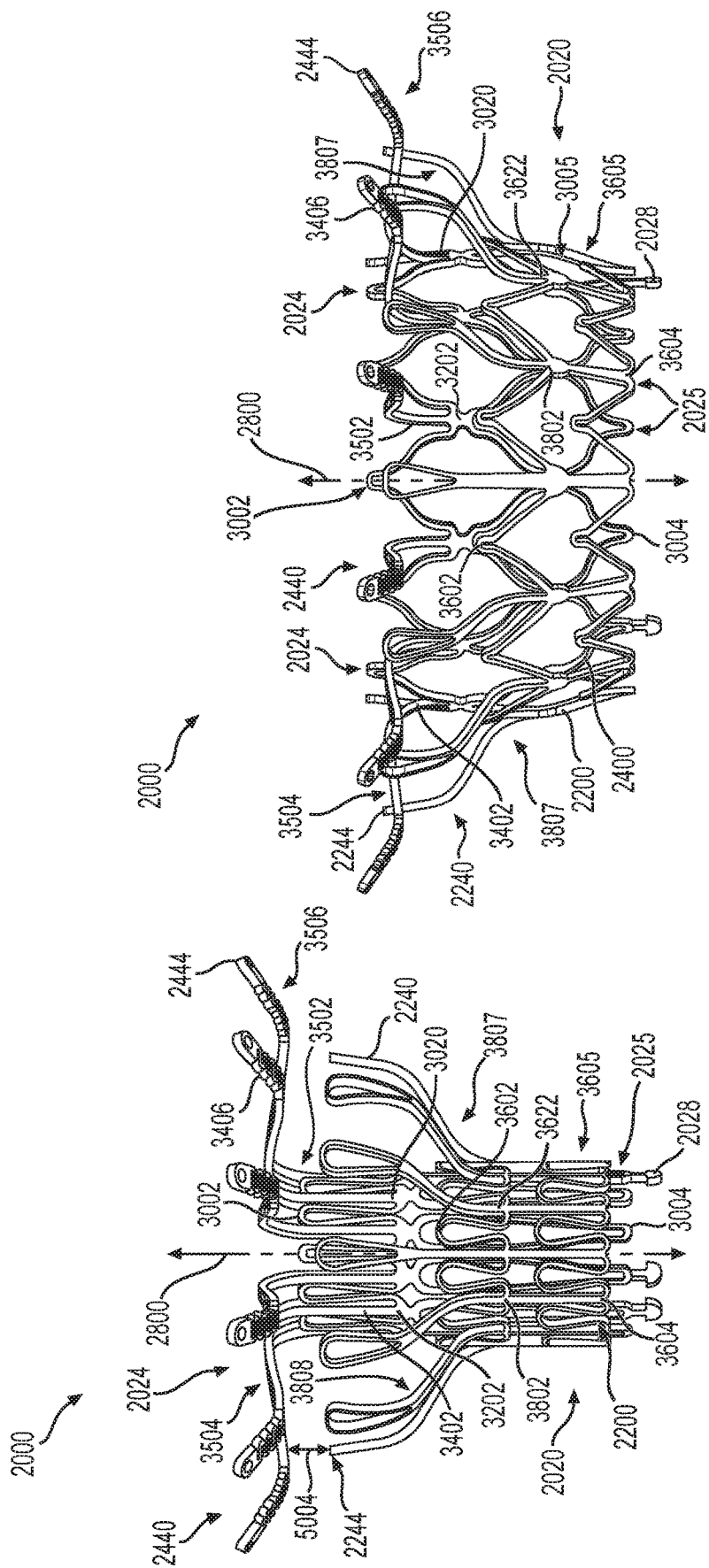

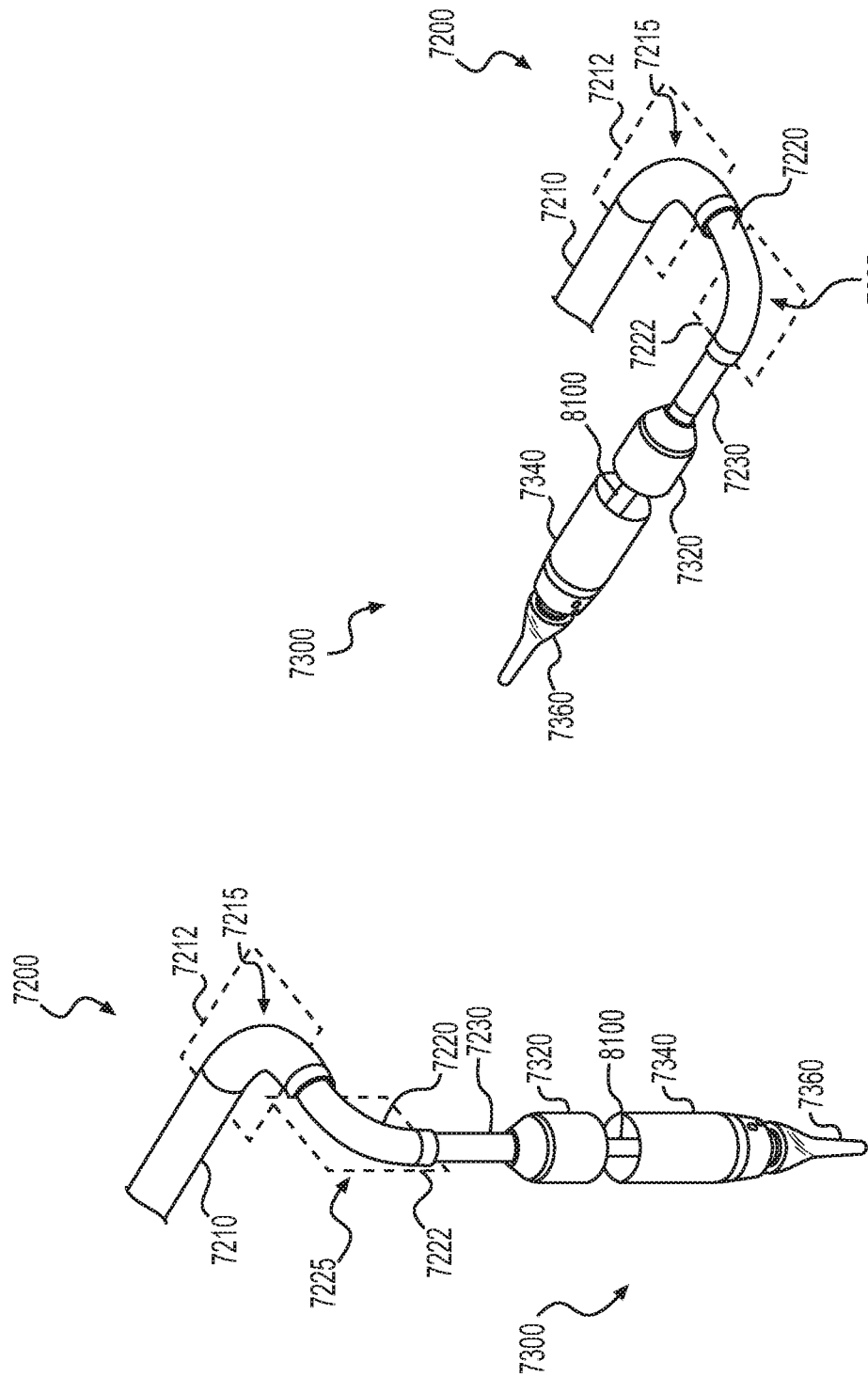

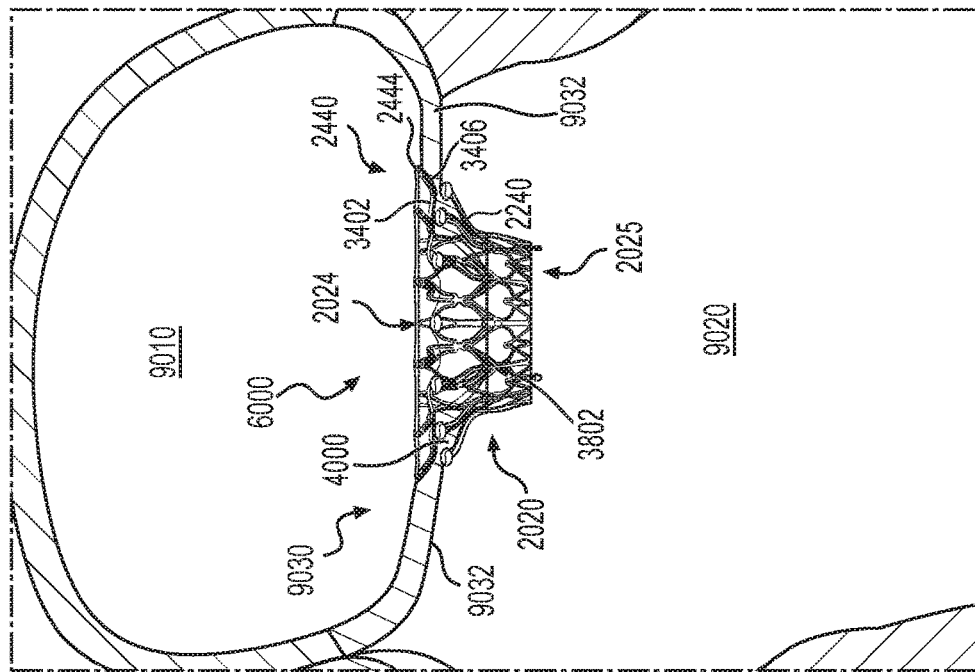
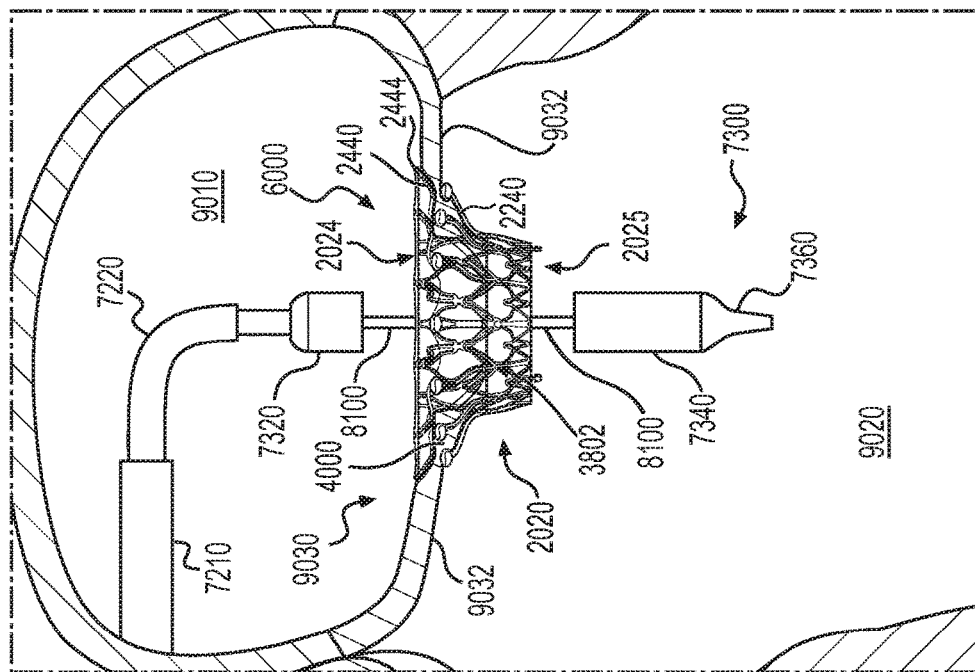

HEART VALVE DELIVERY SYSTEMS AND METHODS

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to delivery systems for implantation of prosthetic valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired, such as due to cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size yet still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit lower protrusion into the chambers of the heart. The present disclosure also provides improved prosthetic heart valve delivery systems and methods of implanting prosthetic heart valves therewith, such that prosthetic heart valves may be securely anchored at the implantation site.

SUMMARY

Disclosed herein are systems and methods for implantation of prosthetic valves by prosthetic valve delivery systems. Particular examples of the disclosure may pertain to a prosthetic valve delivery system having multiple adjustable flexure radii and a capsule configured to retain a prosthetic valve therein.

According to an exemplary embodiment of the present disclosure, a heart valve delivery system is provided. The heart valve delivery system includes at least a first catheter, a second catheter, and a third catheter arranged in a telescoping configuration. The first catheter is movable relative to the second catheter and the third catheter. The first catheter extends from the distal end of the second catheter by a variable distance of between 0 and 20 centimeters. The second catheter is movable relative to the third catheter and extends from the distal end of the third catheter. The heart valve delivery system includes a first adjustable flexure radius associated with the second catheter, the first flexure radius being located within five centimeters of the distal end of the second catheter. The heart valve delivery system includes a second adjustable flexure radius associated with the third catheter, the second flexure radius configured to be adjusted independently of the first flexure radius. The heart valve delivery system includes a capsule secured to the first catheter and an ejector associated with the capsule. The heart valve delivery system includes at one control handle assembly configured to permit at least two of the catheters to rotate together, to independently adjust the first and second flexure radii, to cause relative axial movement between the catheters, and to permit the ejector to cause relative movement between a heart valve and the capsule.

In some embodiments, the capsule includes an atrial capsule portion and a ventricular capsule portion, the atrial capsule portion and the ventricular capsule portion being configured for relative longitudinal movement. The ventricular capsule portion is configured to retain an annular valve body of the heart valve and a plurality of ventricular anchoring legs of the heart valve therein. The atrial capsule portion is configured to retain a plurality of atrial anchoring arms of the heart valve therein. The capsule includes a valve anchor configured to engage the annular valve body of the heart valve, the ejector being configured to release the annular valve body from engagement with the valve anchor. The ejector is further configured to effect movement between the capsule and the plurality of ventricular anchoring legs while the annular valve body remains engaged with the valve anchor.

In some embodiments, an axial length of the ventricular capsule portion is at least twice as long as an axial length of the atrial capsule portion. The control handle assembly is configured to assume a capsule lock configuration in which the ejector is prevented from moving the ventricular capsule portion beyond a pre-determined location, and a capsule release configuration in which the ejector is permitted to move the ventricular capsule portion beyond the pre-determined location.

In some embodiments, the ejector is situated at least partially within the first catheter. The control handle assembly includes a guide actuator configured to effect movement of the second catheter, a sheath actuator configured to effect movement of the third catheter, and a capsule handle configured to control the ejector. The guide actuator, the sheath actuator, and the capsule handle are configured for relative longitudinal movement. The capsule handle includes a first release actuator configured to control relative movement between a first portion of the capsule and the heart valve, while the heart valve remains longitudinally fixed relative to the first catheter. The capsule handle includes a second release actuator configured to control release of the heart valve from the capsule by the ejector. The capsule handle is configured to assume an anchoring configuration in which the second release actuator is prevented from controlling the ejector to release the heart valve from the capsule, and a final release configuration in which the second release actuator is permitted to control the ejector to release the heart valve from the capsule. The second release actuator is configured to control relative movement between a second portion of the capsule and the heart valve while the capsule handle is in the anchoring configuration. The capsule handle includes a slide lock configured to assume a locked position in which longitudinal movement of the first catheter is prevented, the capsule being configured for longitudinal movement relative to the first catheter when the slide lock is in the locked position.

In some embodiments, the control handle assembly is further configured to prevent relative longitudinal movement between the first catheter and the second catheter. The control handle assembly is further configured to steer the first catheter independently of adjustment of the first and second flexure radii. The second flexure radius is configured to remain substantially straightened while the first flexure radius is adjusted. The first flexure radius and the second flexure radius are each configured to be adjusted by an angle greater than 90°. In some embodiments, the first flexure radius and the second flexure radius are each configured to be adjusted by 120°. In some embodiments, the first flexure radius and the second flexure radius are configured to bend the first catheter by an angle greater than 180°. In some embodiments, the first catheter is configured to advance the heart valve within a heart chamber while the second catheter and third catheter remain stationary relative to the heart chamber.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 4A illustrates a cross-sectional view of the exemplary frame of FIG. 2A, consistent with various embodiments of the present disclosure.

FIG. 4B illustrates an enlarged view of a volume between an atrial anchoring arm and a ventricular anchoring leg of the exemplary frame of FIG. 4A, consistent with various embodiments of the present disclosure.

FIGS. 5A-5E illustrate structural changes in the exemplary frame of FIG. 2A during transitioning of the frame between a radially-contracted configuration and a radially-expanded configuration, consistent with various embodiments of the present disclosure.

FIG. 7C illustrates an exemplary configuration of a telescoping catheter assembly and the delivery capsule of the exemplary prosthetic valve delivery system of FIG. 7A, consistent with various embodiments of the present disclosure.

FIG. 7D illustrates another exemplary configuration of the telescoping catheter assembly and delivery capsule of FIG. 7C, consistent with various embodiments of the present disclosure.

FIGS. 10A-10H depict implantation of the prosthetic valve of FIGS. 6A-6E within a native mitral valve by the exemplary prosthetic valve delivery system of FIG. 7A, consistent with various embodiments of the present disclosure.

DETAILED DESCRIPTION

Figure 1A:
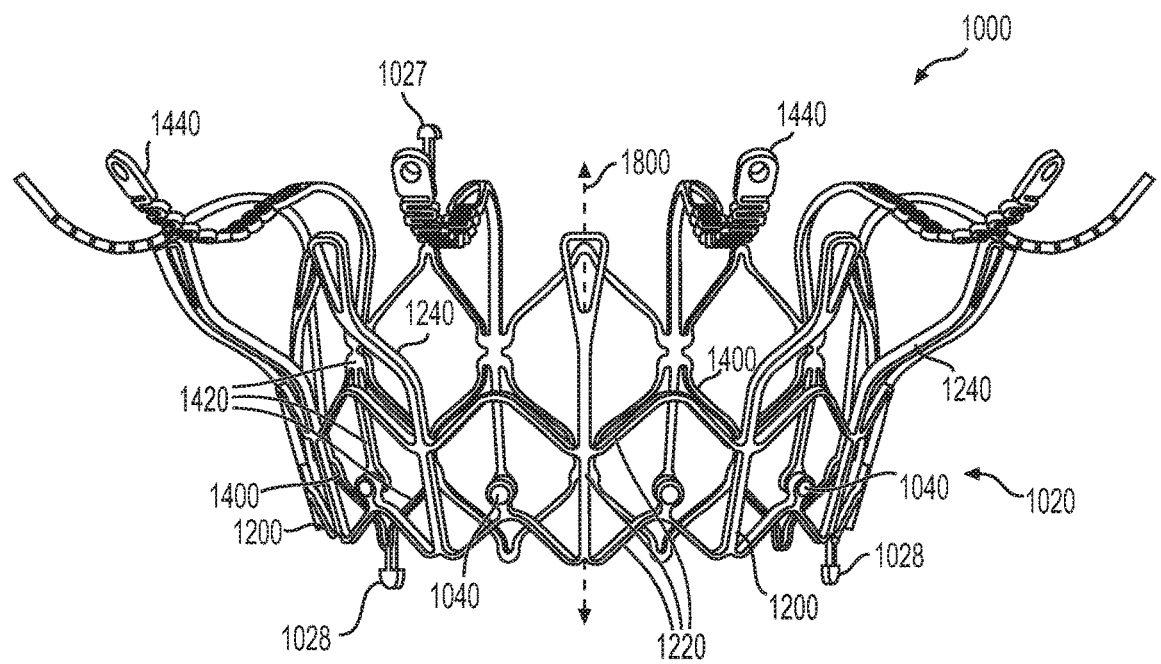
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
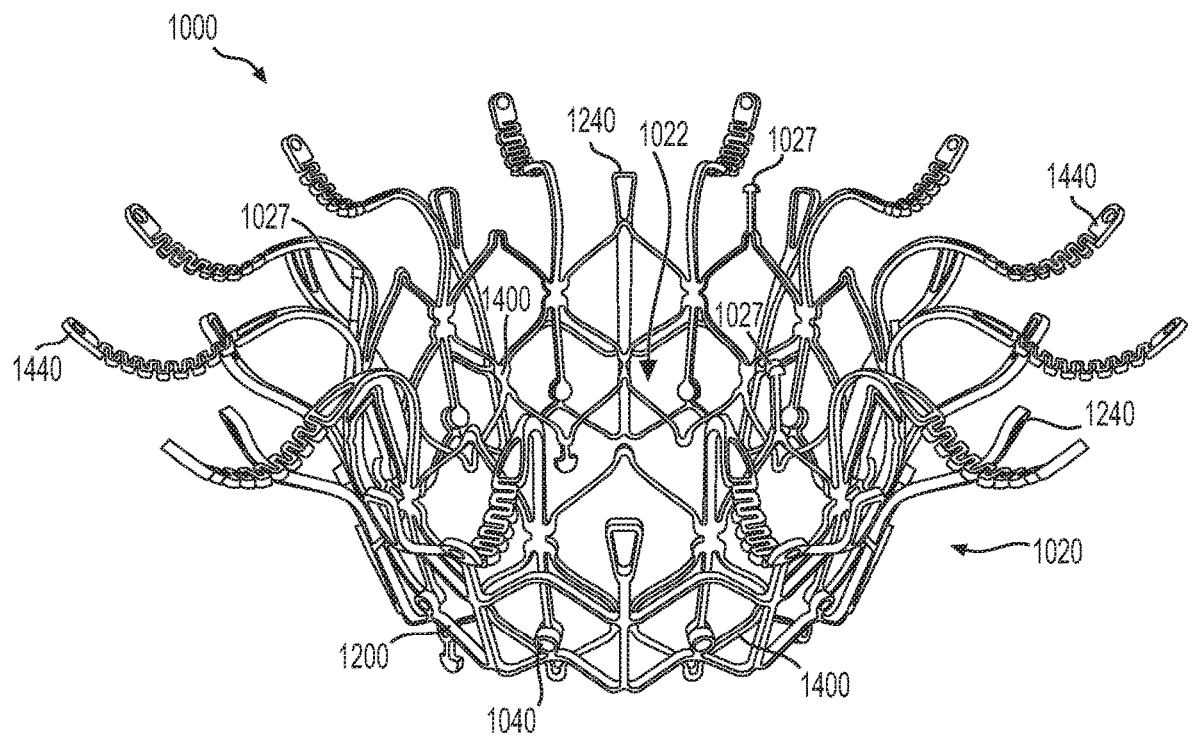
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
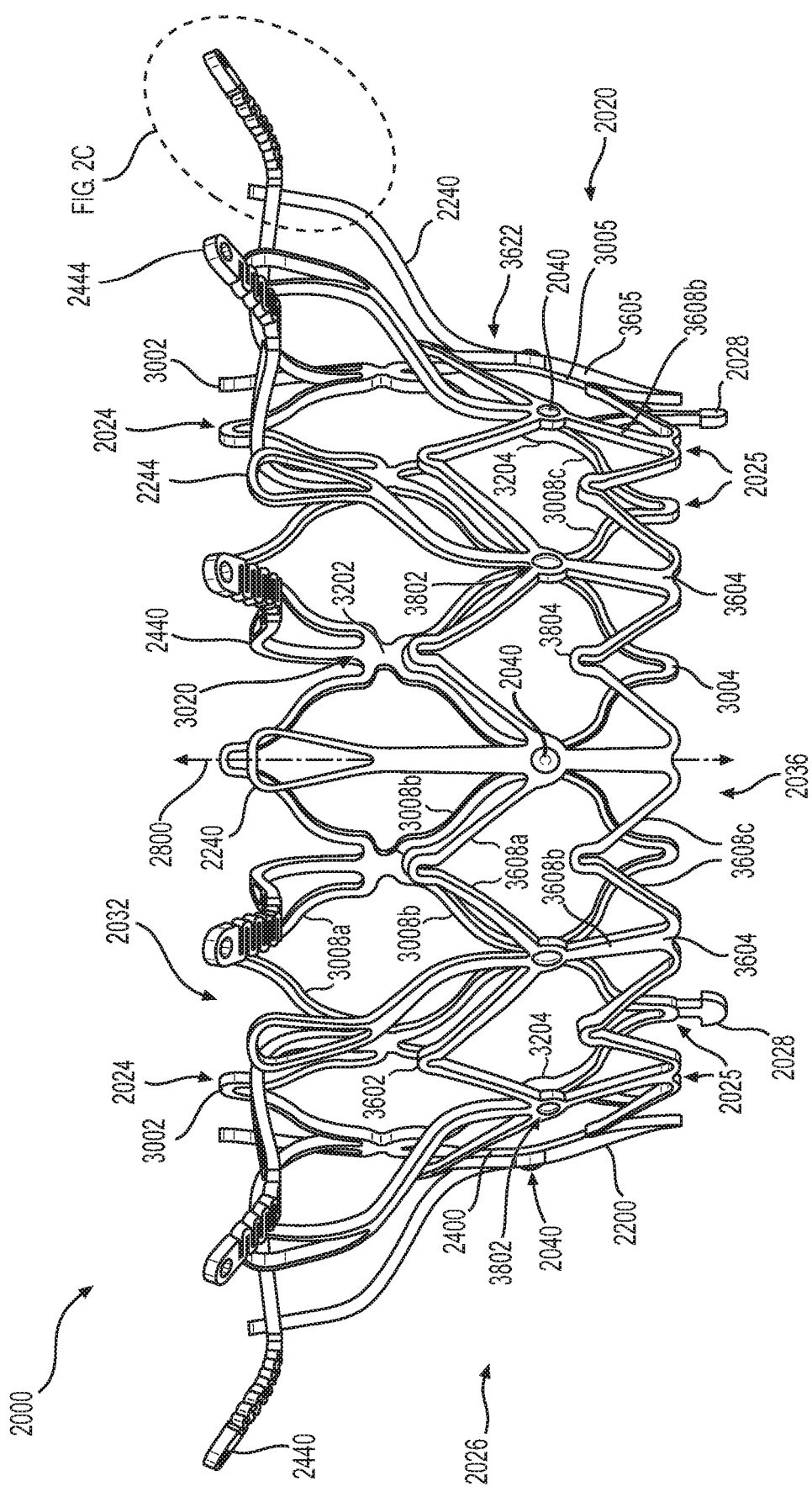
FIG. 2A illustrates a front elevation view of another exemplary frame for a prosthetic valve, consistent with various embodiments of the present disclosure.
Figure 2B:
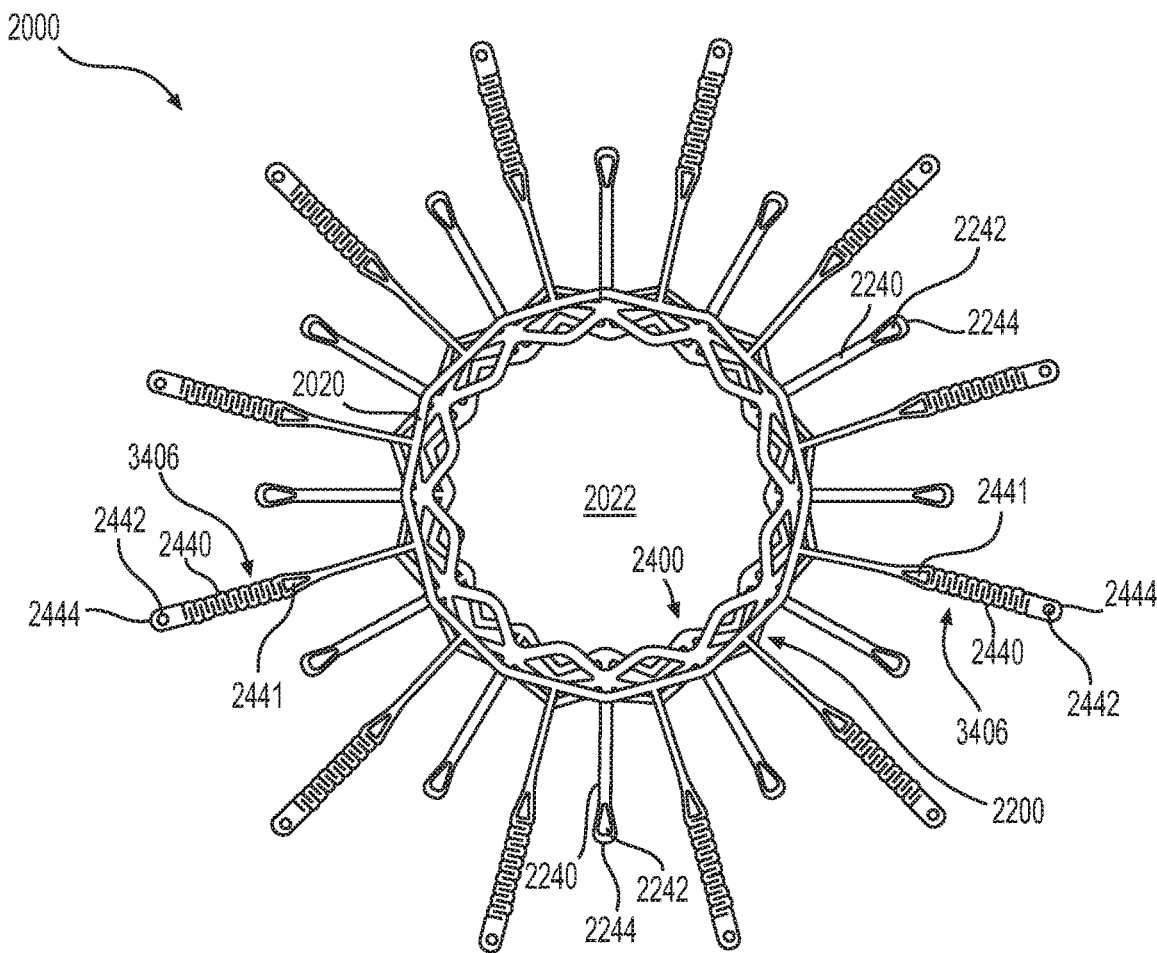
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrium, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
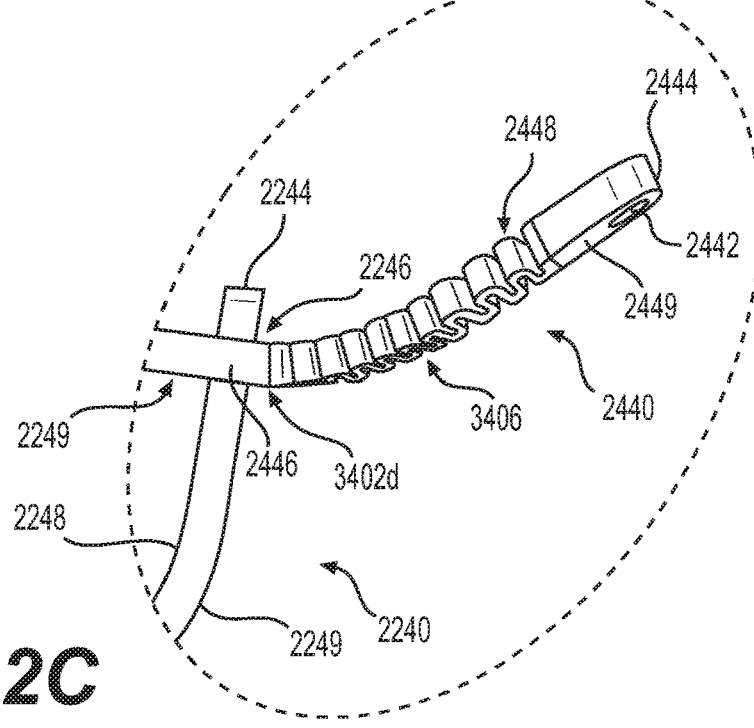
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
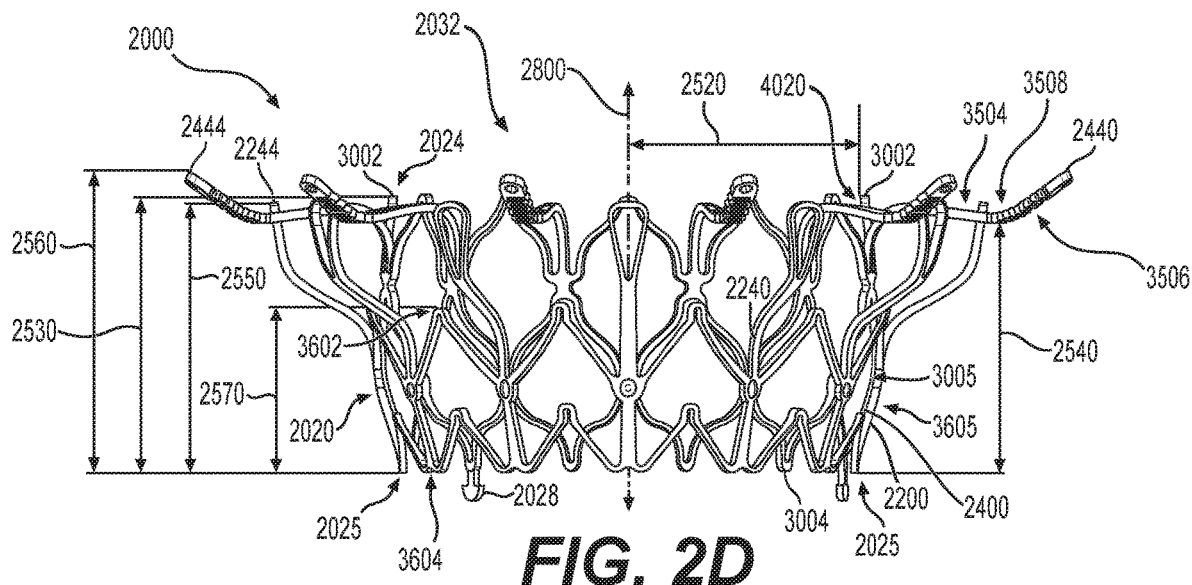
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
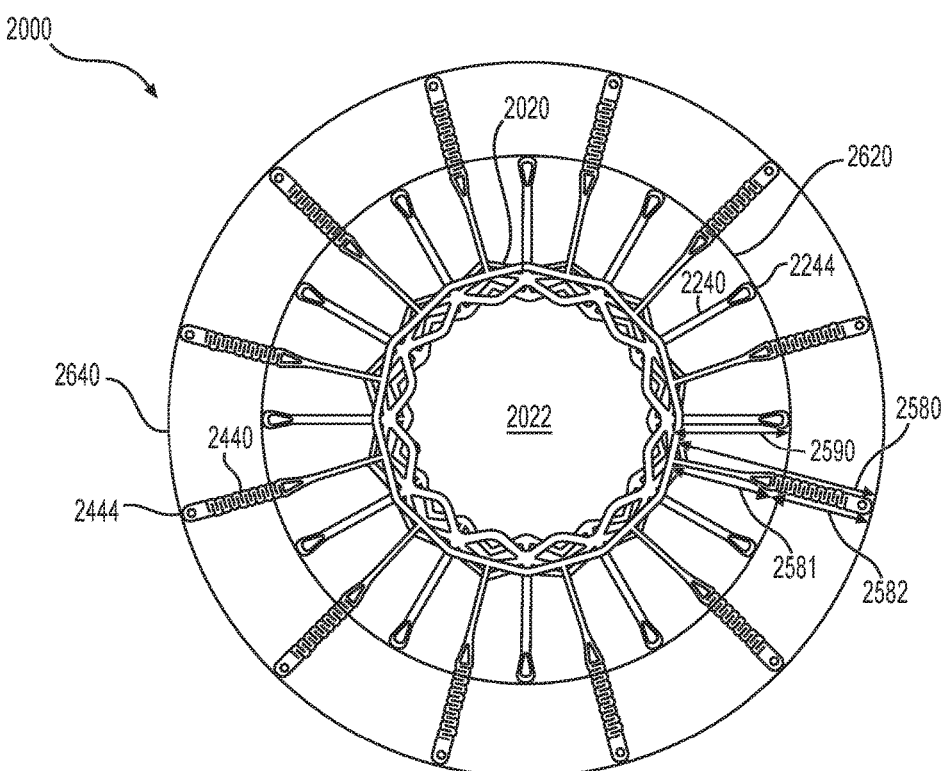
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
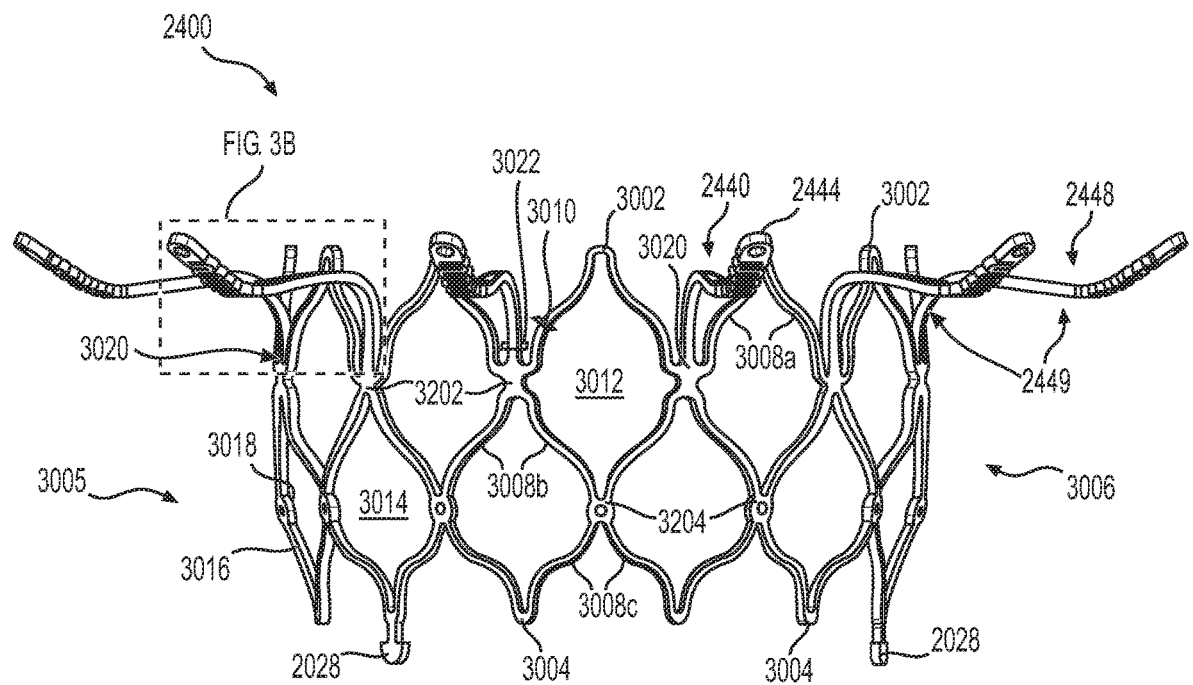
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
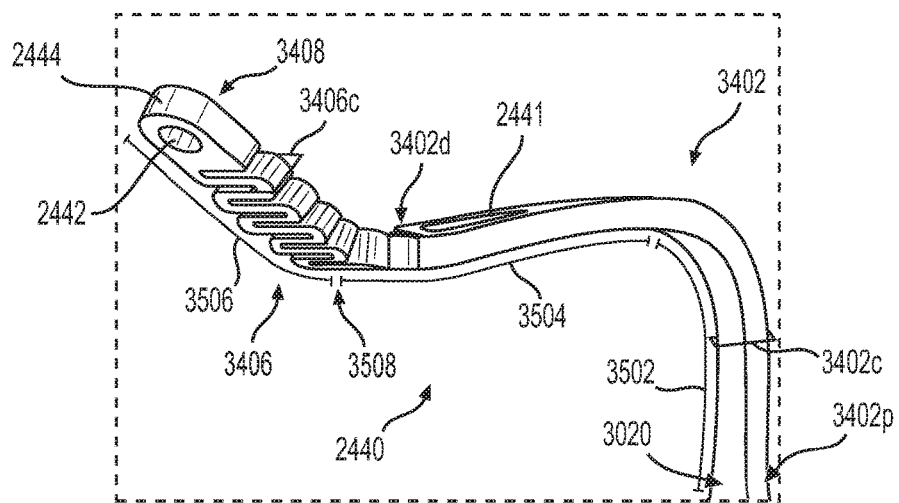
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
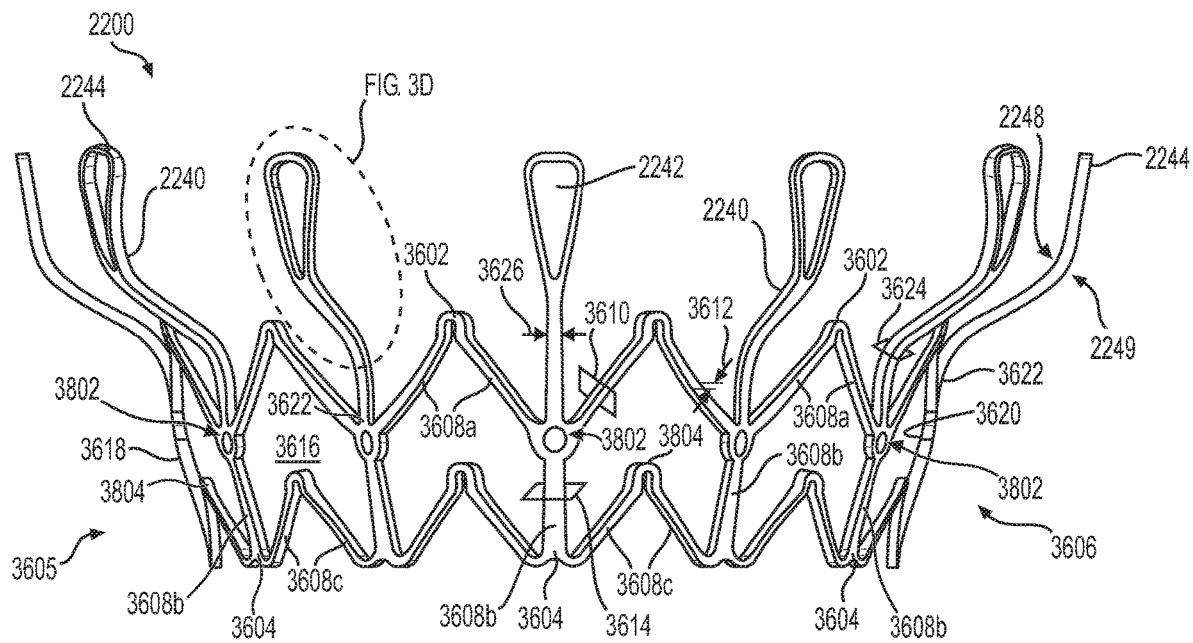
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
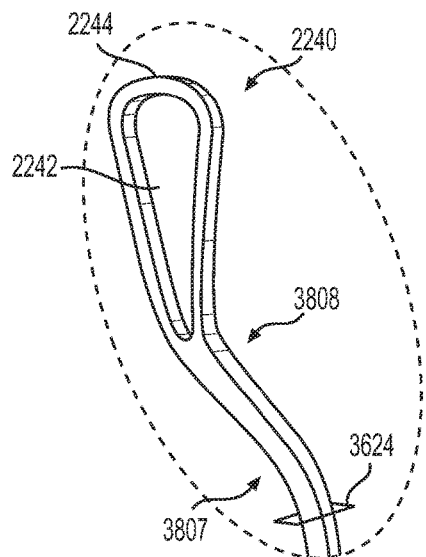
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
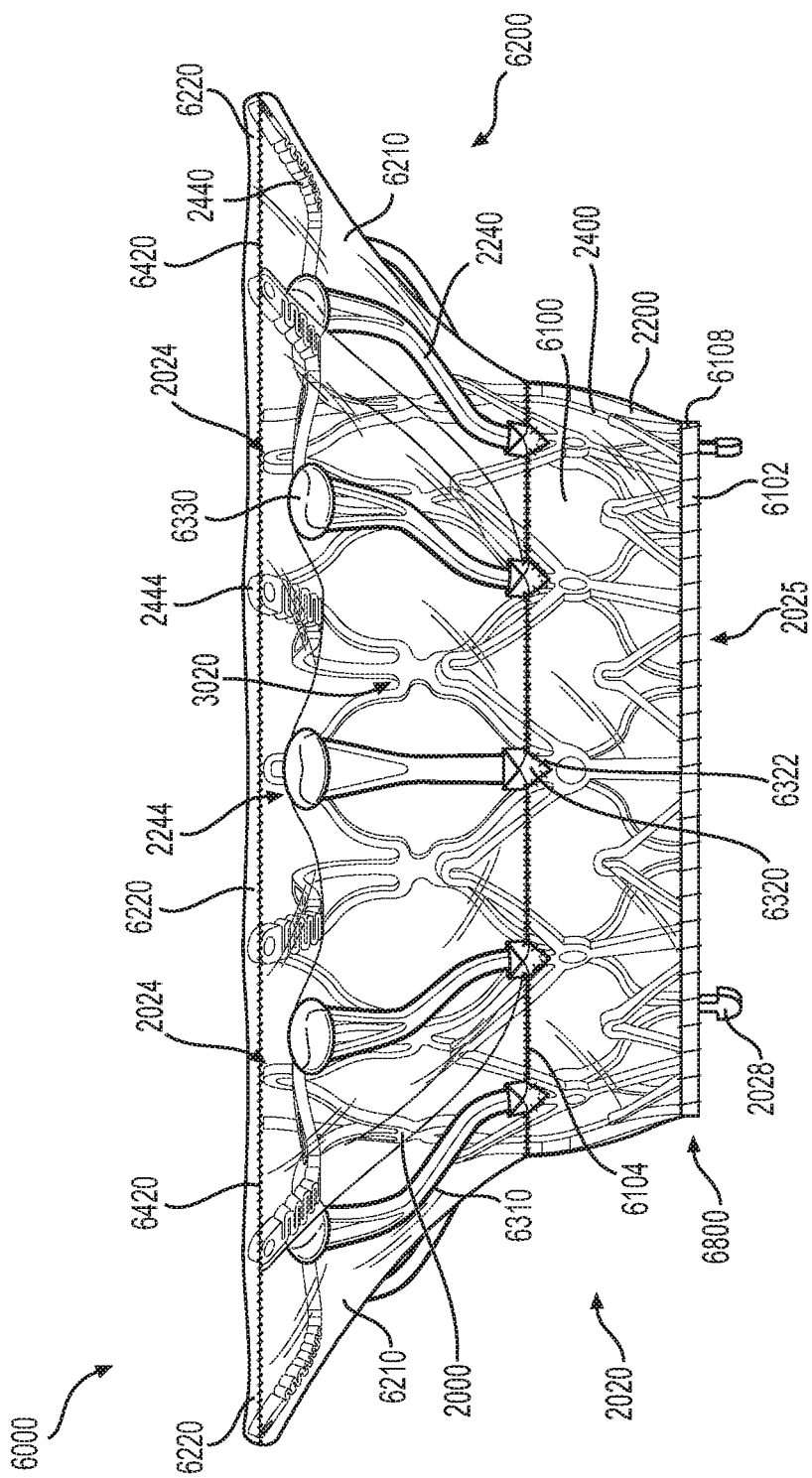
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
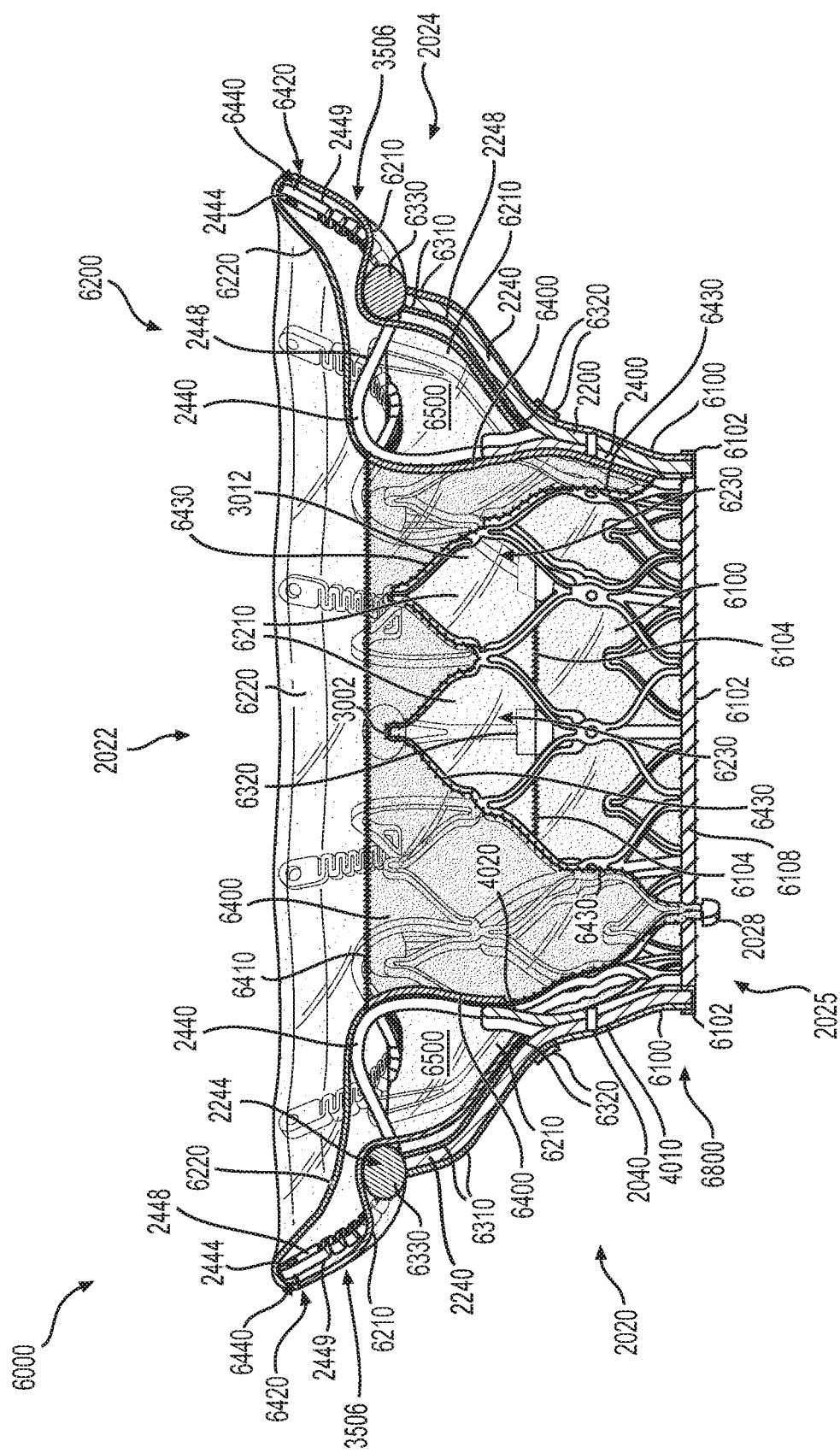
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
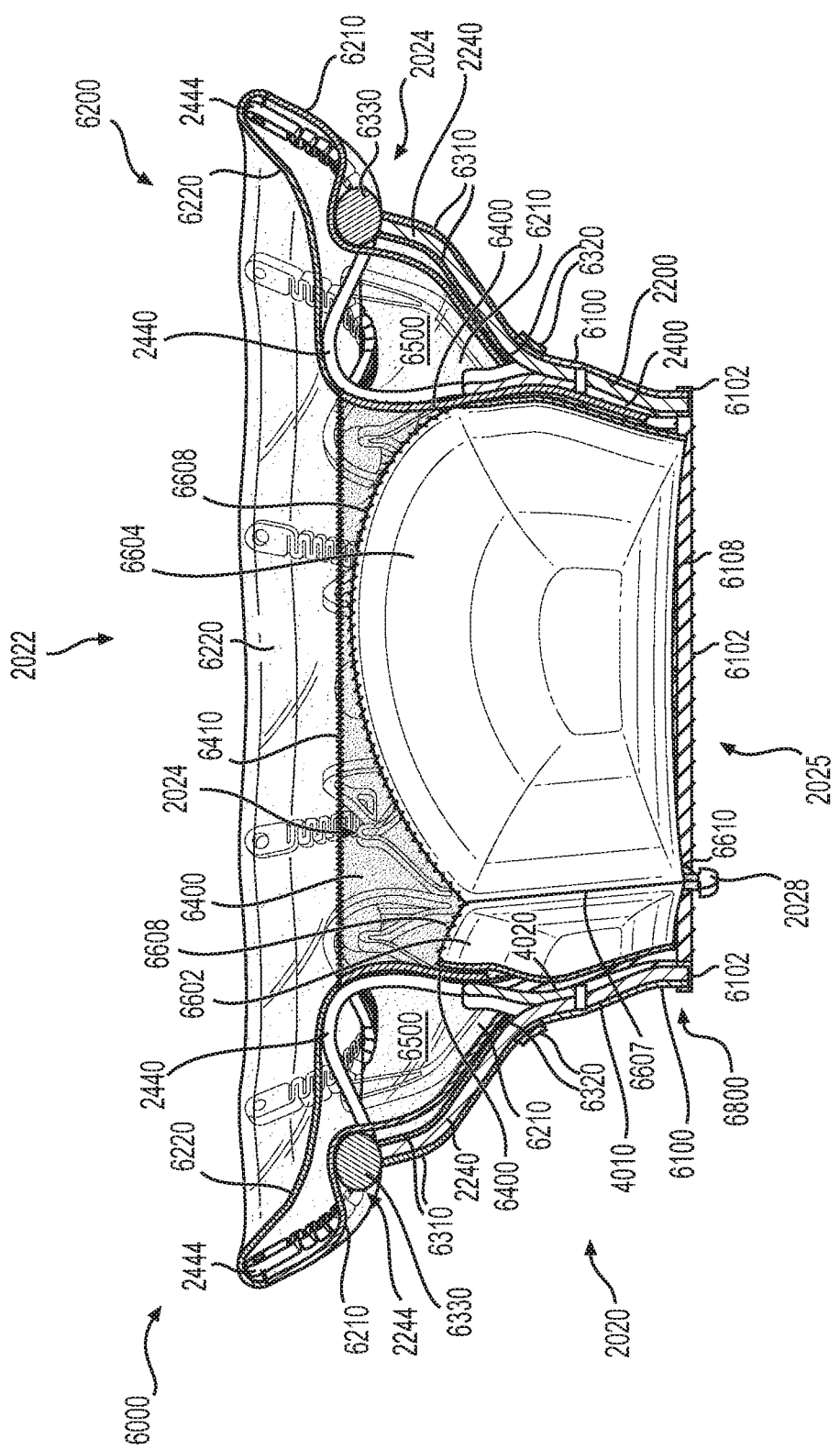
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
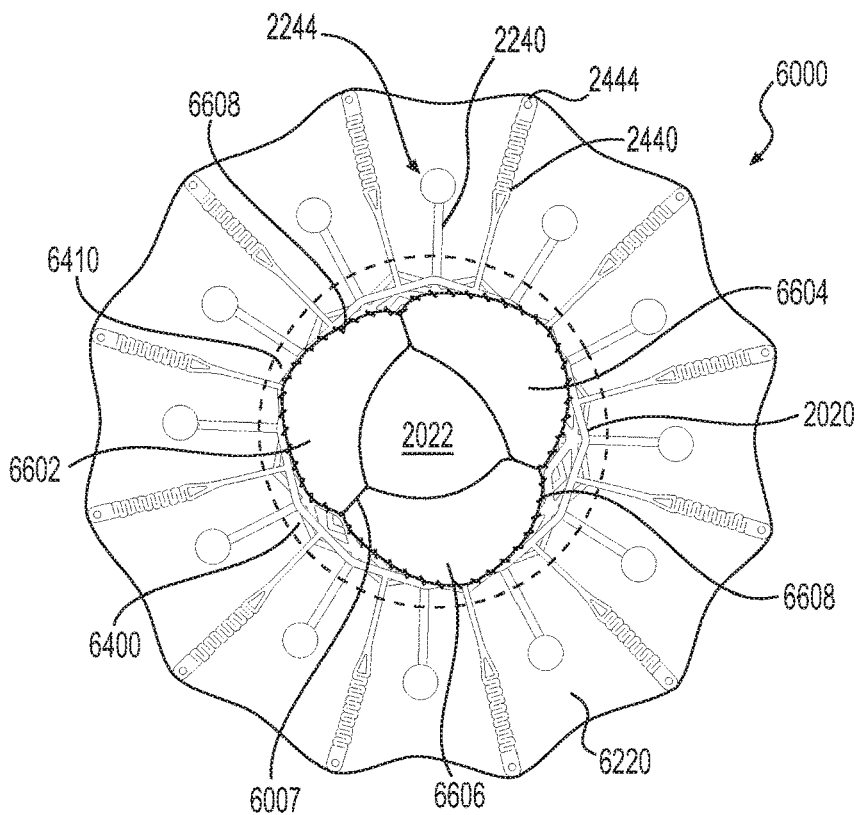
FIG. 6D illustrates a top plan view of the exemplary prosthetic valve of FIG. 6A with uninflated leaflets, consistent with various embodiments of the present disclosure.
Figure 6E:
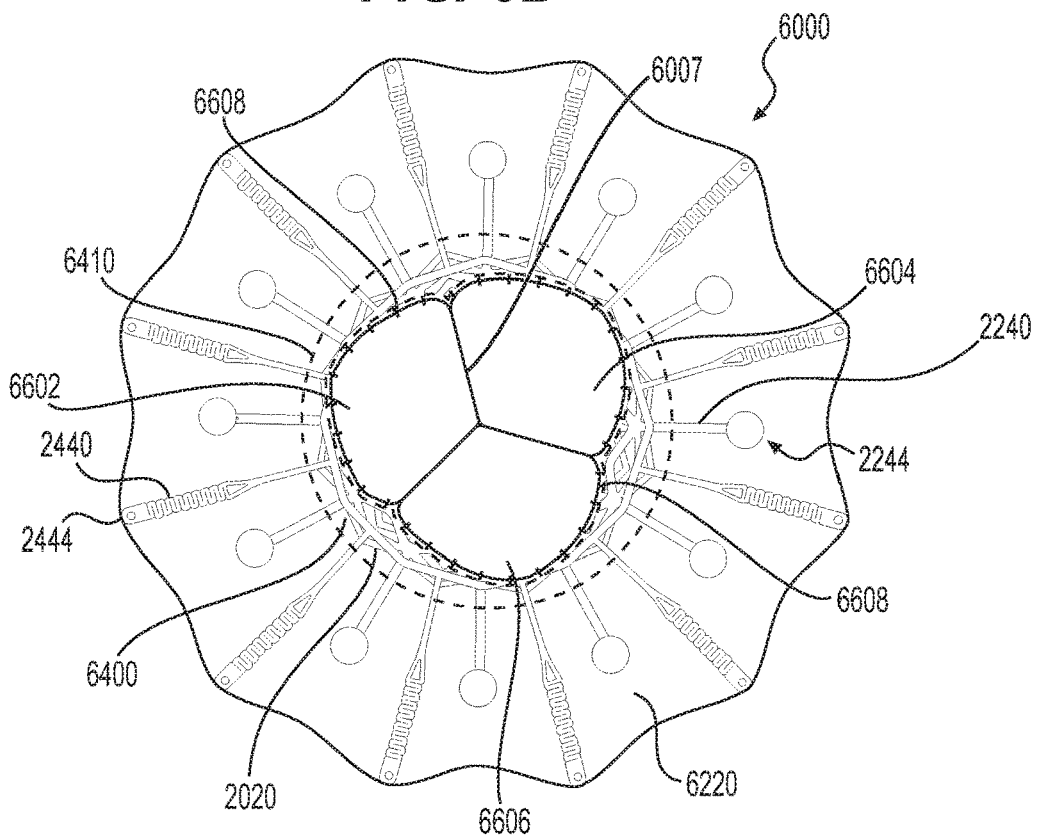
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
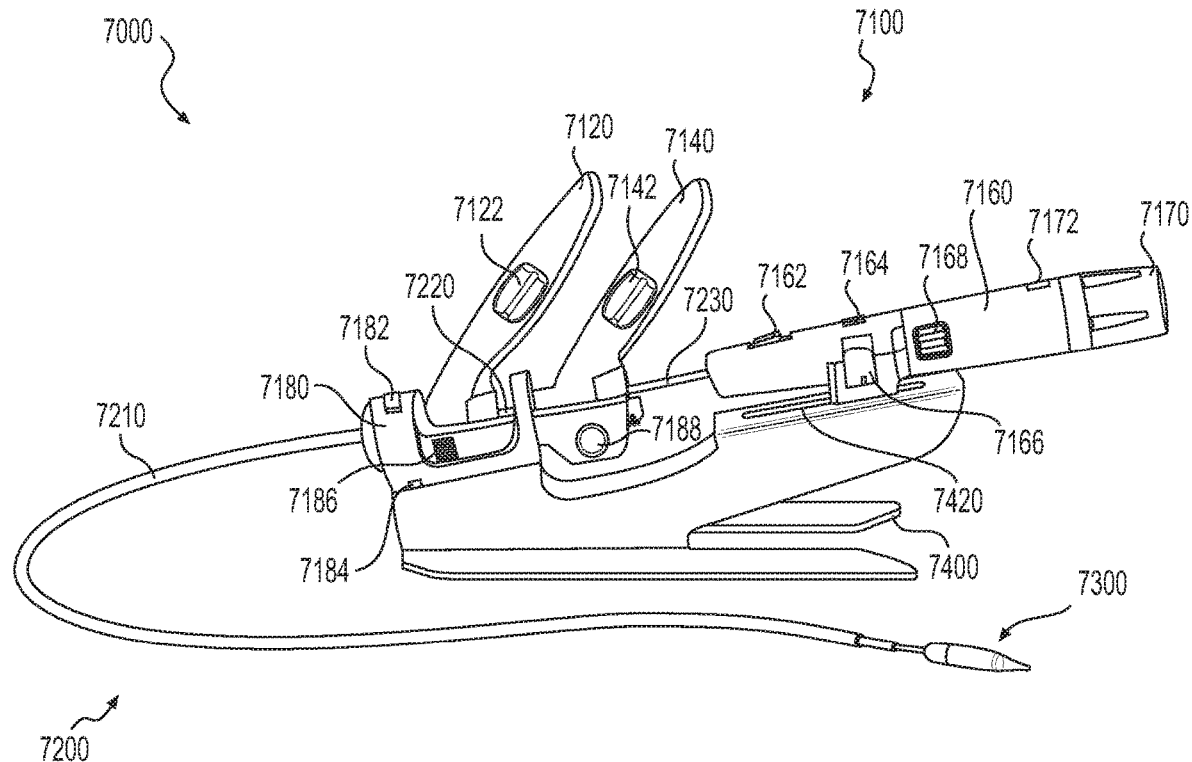
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
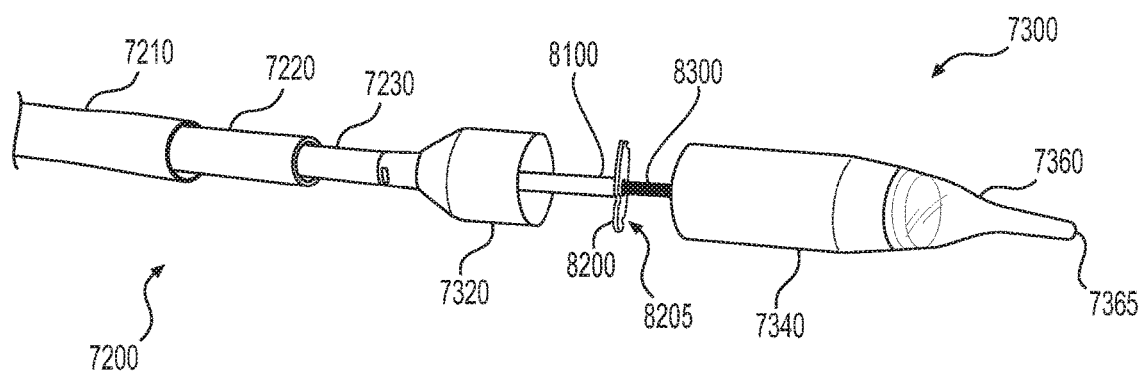
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
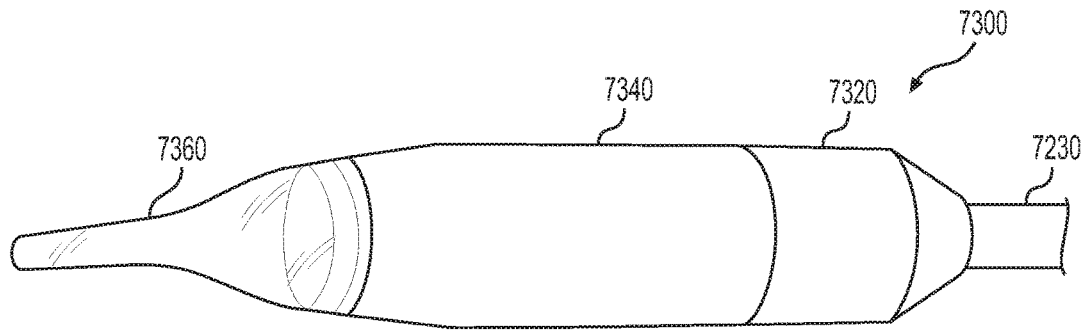
FIG. 8A illustrates another enlarged view of the exemplary delivery capsule of the prosthetic valve delivery system of FIG. 7A in a closed configuration, consistent with various embodiments of the present disclosure.
Figure 8B:
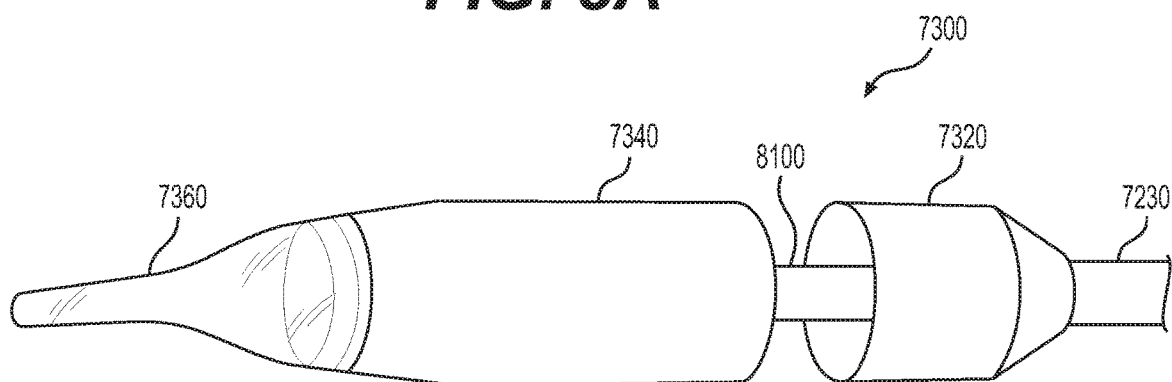
FIG. 8B illustrates the exemplary delivery capsule of FIG. 8A in an open configuration, consistent with various embodiments of the present disclosure.
Figure 8C:
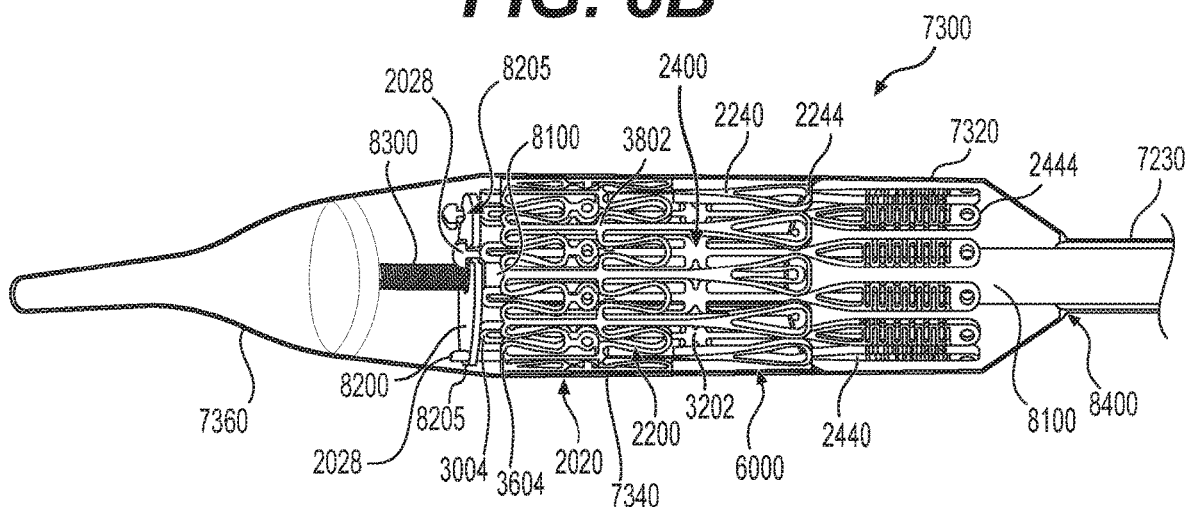
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
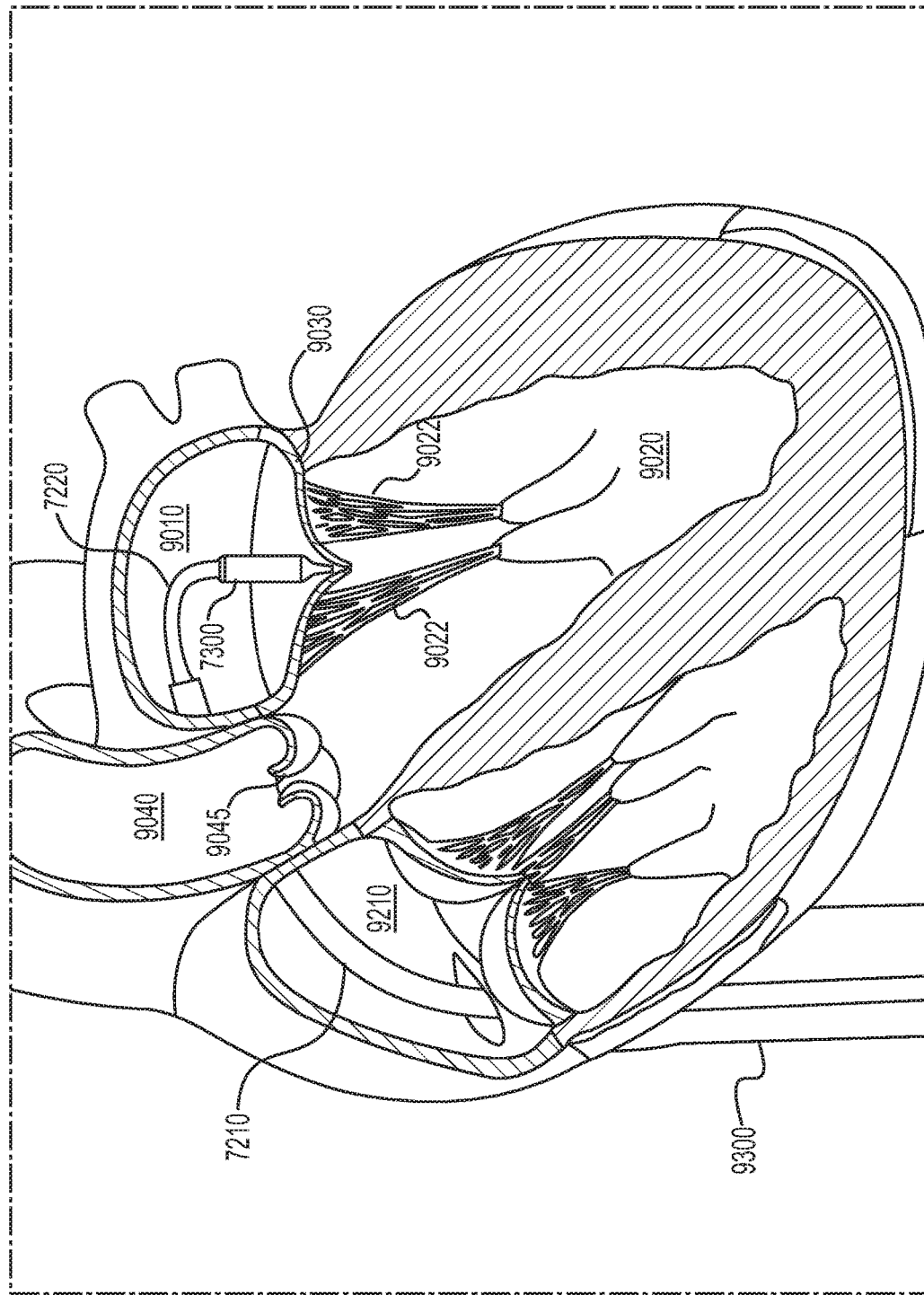
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10A:
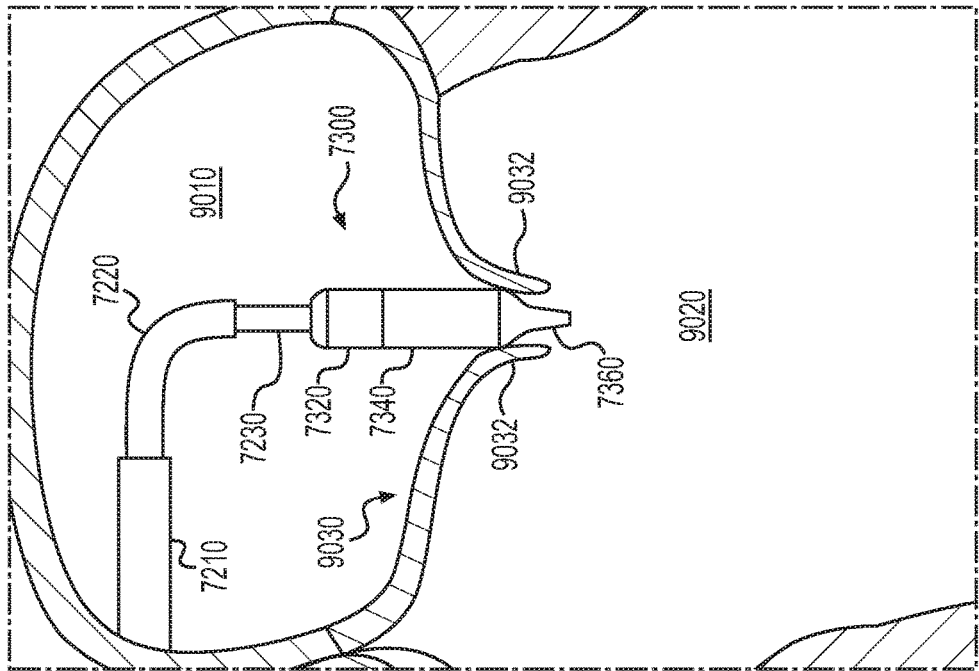
Figure 10B:
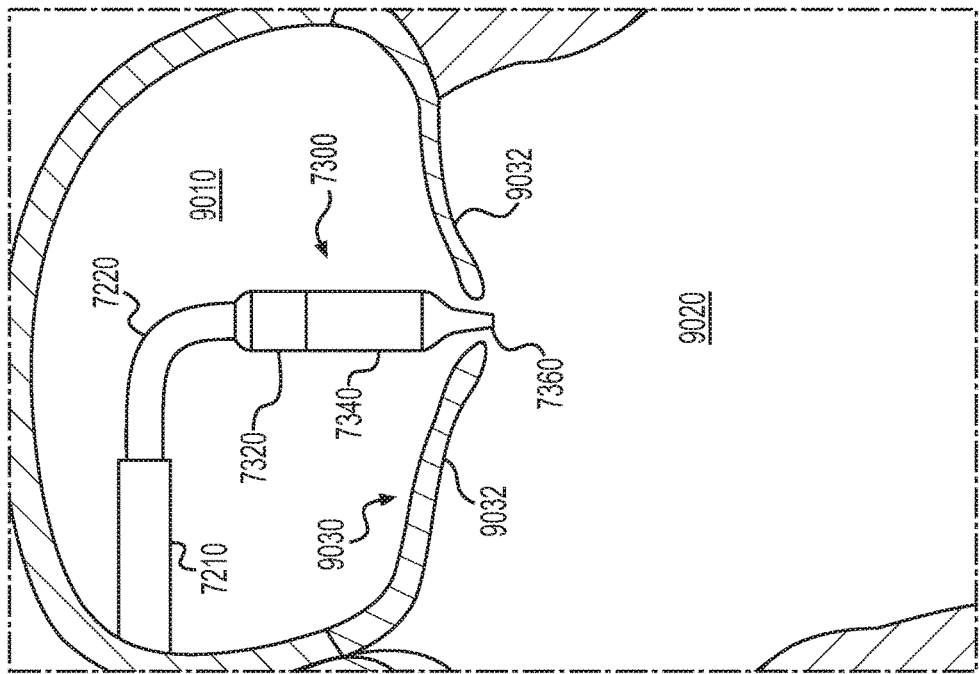
Figure 10D:
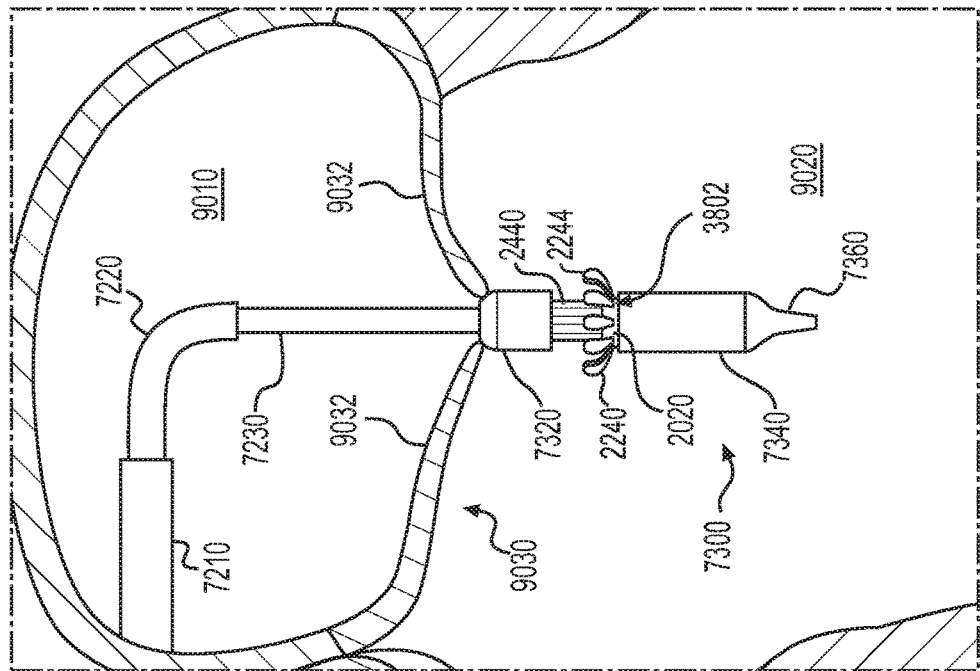
Figure 10C:
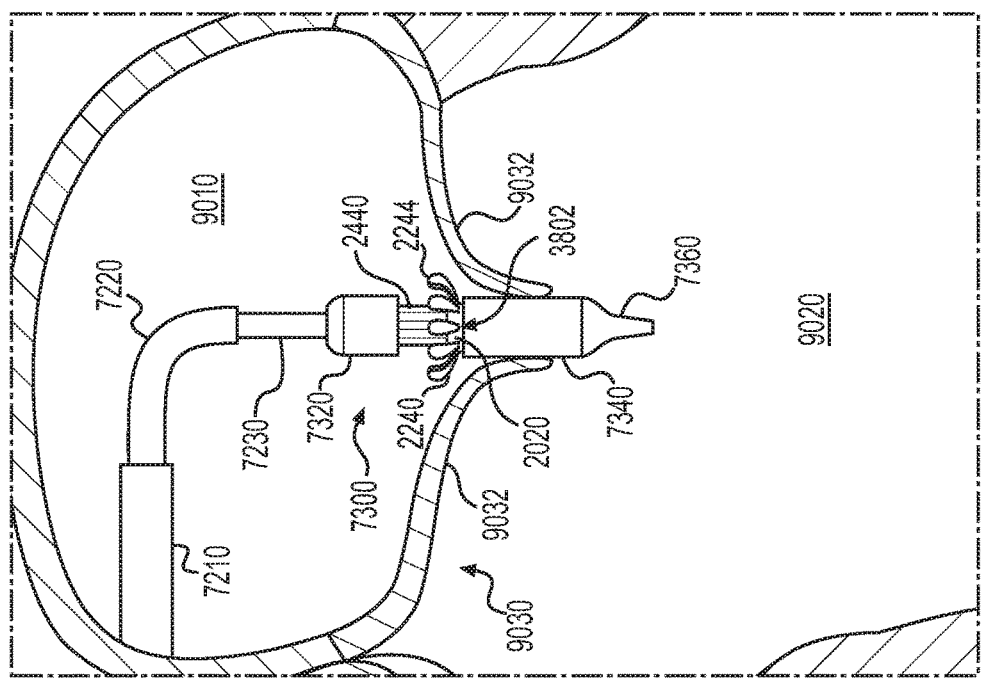

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
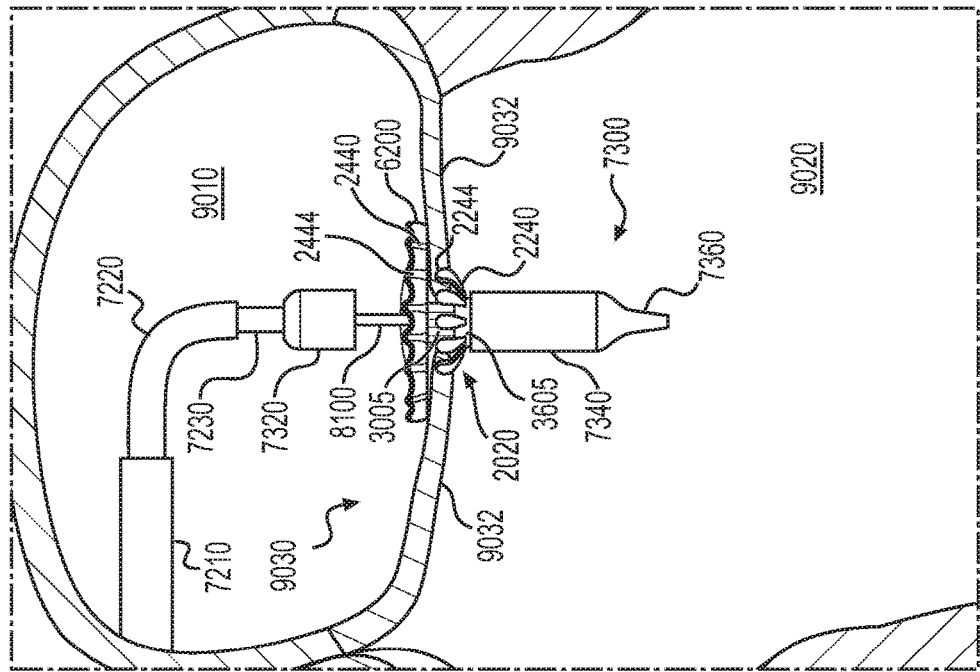
Figure 10E:
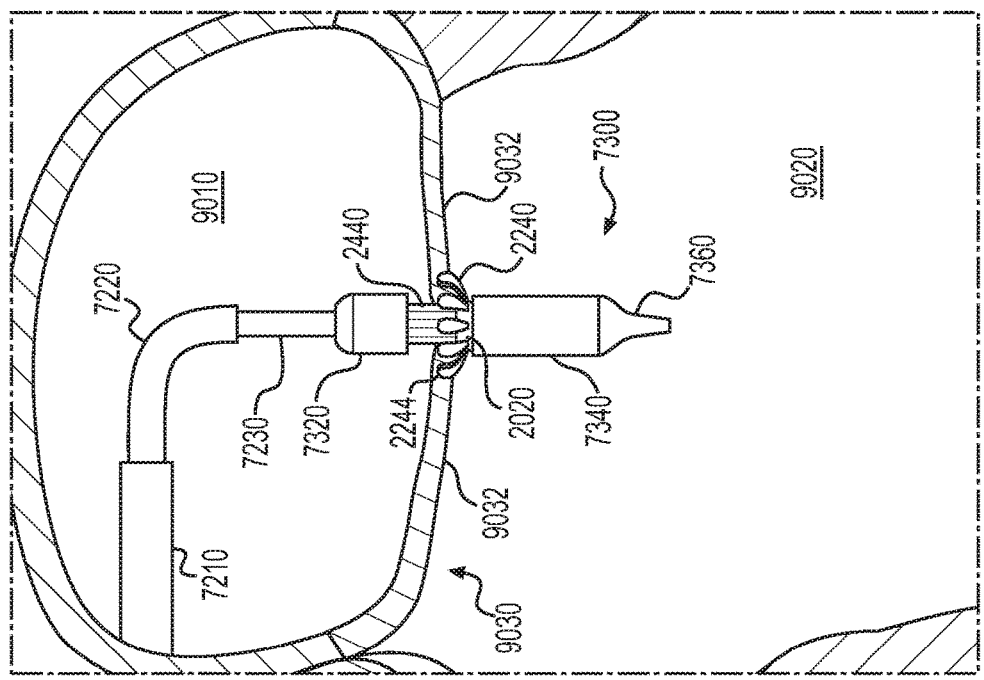

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to heart valve delivery systems. While the present disclosure provides examples of heart valve delivery systems, it should be noted that aspects of the disclosure in their broadest sense, are not limited to heart valve delivery systems. Rather, it is contemplated that aspects of the present disclosure may be applied to delivery systems for other prosthetic or implantable devices as well and are not limited to delivery systems for heart valves, prosthetic valves, or cardiac valves. Prosthetic valve delivery system 7000 illustrated in FIG. 7A is one example of a heart valve delivery system in accordance with this disclosure.

An exemplary heart valve delivery system in accordance with the present disclosure may include one or more catheters configured to approach the heart transfemorally, transapically, transatrially, transseptally, or transjugularly. The one or more catheters may be configured to position the heart valve, which may be retained within the delivery system, in or near the native valve orifice such that the heart valve may be released from the delivery system within or near the native valve. As used herein, the term "catheter" may denote an elongated, tubular structure that may be selectively flexible along a length of the elongated structure. The one or more catheters can be manufactured from a variety of suitable, biocompatible materials, some non-limiting examples including silicone, Pebax, rubber, nylon, polyurethane, polyethylene terephthalate (PET), latex, thermoplastic elastomers, silicone, and polyimides. The one or more catheters may be sufficiently flexible such that they may be configured to pass through tortuous anatomy (e.g., blood vessels and heart chambers) without sustaining damage or injuring the native tissue during delivery of the catheter to the implantation site. The one or more catheters of the exemplary heart valve delivery system may be at least long enough to extend from a location outside of a patient's body to a site within the heart. The one or more catheters may be configured as a one-size-fits all, a range of sizes depending on the size of the patient or may be fully customizable. Exemplary sizes of the one or more catheters may include between 6 French (Fr) and 40 Fr, between 20 Fr and 35 Fr, or between 27 Fr and 33 Fr. The one or more catheters may have any appropriate length, for example between 1 millimeter (mm) and 1 meter (m), between 1 mm and 2 m, between 1 mm and 3 m, or longer, such that the one or more catheters are at least long enough to extend from a location outside of the patient's body to a site within the heart.

In some embodiments, the one or more catheters of the exemplary heart valve delivery system may include at least a first catheter, a second catheter, and a third catheter, which may be arranged in a telescoping configuration. In some embodiments, the first catheter may be the inner-most catheter of the delivery system. Alternatively, the first catheter may receive another catheter or tubular structure therein. In some embodiments, the first catheter may be coaxially arranged within the second catheter. Additionally, or alternatively, the second catheter may be coaxially arranged within the third catheter, and the third catheter may be the outer-most catheter of the delivery system. Alternatively, the third catheter may be received within another catheter or tubular structure. The term "telescoping configuration" may refer to the coaxial arrangement of the first, second, and third catheters, where the first catheter is coaxially arranged within the second catheter, and the second catheter is coaxially arranged within the third catheter, thereby creating the exemplary telescoping configuration.

FIGS. 7A-7B, for example, illustrate an exemplary prosthetic valve delivery system 7000, which may include an implant catheter 8100 coaxially arranged within a guide catheter 7220, as part of a telescoping catheter assembly 7200. Accordingly, implant catheter 8100 may constitute a first catheter of prosthetic valve delivery system 7000. Optionally, implant catheter 8100 may be coaxially arranged within a capsule shaft 7230, which may in turn be arranged within guide catheter 7220. Guide catheter 7220 may be coaxially arranged within an outer sheath 7210, as part of the telescoping catheter assembly 7200. Accordingly, guide catheter 7220 may constitute a second catheter of prosthetic valve delivery system 7000. Outer sheath 7210 illustrated in FIG. 7B is one example of a third catheter of delivery system 7000, in accordance with various embodiments of the present disclosure. Outer sheath 7210 may form a portion of telescoping catheter assembly 7200 of delivery system 7000. Accordingly, outer sheath 7210 may constitute a third catheter of the prosthetic valve delivery system 7000. As illustrated in FIG. 7A, telescoping catheter assembly 7200 may extend between and form a physical connection between control handle assembly 7100 and capsule 7300 and may include a plurality of telescoping catheters (including outer sheath 7210).

In some embodiments, the first catheter may be movable relative to one or both of the second catheter and the third catheter. The term "movable" may refer to the ability for one or both of longitudinal movement and rotation of the first catheter relative to one or both of the second catheter and the third catheter and may constitute movement away from and/or towards the second catheter and the third catheter. For example, the first catheter may selectively move longitudinally away (i.e., in the distal direction) from the second catheter and the third catheter. FIGS. 10F and 10G illustrate an example of an outer sheath 7210 (i.e., the exemplary third catheter), a guide catheter 7220 (i.e., the exemplary second catheter), and an implant catheter 8100 (i.e., the exemplary first catheter) positioned at longitudinal positions with respect to one another, where implant catheter 8100 (i.e., the exemplary first catheter) moves distally while the guide catheter 7220 and the outer sheath 7210 remain stationary. In this example, stationary second and third catheters may be configured to align implant catheter 8100 with the annulus of the mitral valve 9030, and to provide stability to direct implant catheter 8100 while implant catheter 8100 moves distally.

In an exemplary heart valve delivery system, the first catheter may be configured to extend from the distal end of the second catheter by a variable distance of between zero (0) and twenty (20) centimeters. In some embodiments, the first catheter may extend to any distance between 0 and 20 centimeters; accordingly, the first catheter may extend to a distance of 20 centimeters from the distal end of the second catheter and may extend to any distance until the first catheter reaches 20 centimeters. Alternatively, the first catheter may be configured to assume a pre-determined number of discrete longitudinal positions with respect to the distal end of the second catheter; for example, relative longitudinal movement between the first catheter and the distal end of the second catheter may be affected by a rack and pinion transmission, which may provide a number of discrete stops for the first catheter relative to the second catheter. FIGS. 10F and 10G illustrate an example in which implant catheter 8100 (i.e., the exemplary first catheter) is extended towards ventricle 9020 while the guide catheter 7220 (i.e., the exemplary second catheter) remains stationary; thus, FIGS. 10F and 10G illustrate an embodiment in which implant catheter 8100 is configured to extend a variable distance (e.g., between 0 and 20 centimeters) from the distal end of the guide catheter 7220

In some embodiments, the second catheter is movable relative to the third catheter and extends from the distal end of the third catheter. Accordingly, the second catheter may move longitudinally relative to the third catheter and may constitute movement away from and/or towards the third catheter. For example, the second catheter may selectively move longitudinally away (i.e., in the distal direction) from the distal end of the third catheter.

In some embodiments, the heart valve delivery system may include a first adjustable flexure radius associated with the second catheter. The first flexure radius may be located a distance of between 0.5 centimeters and 8 centimeters from the distal end of the second catheter. Without limitation, for example, the first flexure radius may be located a distance of 0.5 centimeters, 1.0 centimeters, 1.5 centimeters, 2.0 centimeters, 2.5 centimeters, 3.0 centimeters, 3.5 centimeters, 4.0 centimeters, 4.5 centimeters, 5.0 centimeters, 5.5 centimeters, 6.0 centimeters, 6.5 centimeters, 7.0 centimeters, 7.5 centimeters, or 8 centimeters from the distal end of the second catheter. As used herein, the term "adjustable flexure radius" may refer to a portion of a catheter (e.g., the second catheter) configured to bend relative to the rest of the catheter. As used herein, the term "bend" may refer to the shaping or forcing a catheter (e.g., the second catheter) from a straight configuration into a curved or angled configuration, or from a curved or angled configuration to a straight configuration or into a different curved or angled configuration. In some embodiments, the adjustable flexure radius of the second catheter may be configured to bend in a single direction from the straight configuration thereof (e.g., from a straight configuration of the adjustable flexure radius towards a left-hand side, but not towards a right-hand side; referred to hereafter as "unidirectional bending"). In other embodiments, the adjustable flexure radius of the second catheter may be configured to bend in two opposite directions from the straight configuration thereof (e.g., both to the left-hand side and the right-hand side from the straight configuration; referred to hereafter as "bidirectional bending"). In some embodiments, the first flexure radius may be located within 5 centimeters of the distal end of the second catheter such that the first flexure radius may be configured to angle the distal end of the second catheter relative to portions of the second catheter proximal of the first flexure radius. Alternatively, the first flexure radius may be located another suitable distance from the distal end of the second catheter. In some further embodiments, the second catheter may include two or more flexure radii, each of which may be configured for unidirectional bending or bidirectional bending. Bending portion 7225 illustrated in FIGS. 7C and 7D is one example of a first adjustable flexure radius of an exemplary guide catheter 7220, in accordance with the present disclosure. In the example depicted in FIGS. 7C and 7D, bending portion 7225 may be located within 5 centimeters of the distal end of the guide catheter 7220.

In some embodiments, the heart valve delivery system may include a second adjustable flexure radius associated with the third catheter, the second flexure radius may be configured to be adjusted independently of the first flexure radius. In some embodiments, the second adjustable flexure radius of the third catheter may be configured for unidirectional bending. In other embodiments, the second adjustable flexure radius of the third catheter may be configured for bidirectional bending. In some further embodiments, the third catheter may include two or more adjustable flexure radii, each of which may be configured for unidirectional bending or bidirectional bending. Bending portion 7215 illustrated in FIGS. 7C and 7D is one example of a second adjustable flexure radius of an exemplary outer sheath 7210, in accordance with the present disclosure.

In some embodiments, the exemplary heart valve delivery system may include a capsule. In some embodiments, at least a portion of the capsule may be connected to or otherwise secured to the distal end of the first catheter, such that the portion of the capsule and the distal end of the first catheter are secured against relative longitudinal movement. Alternatively, the first catheter may not be secured relative to a portion of the capsule. The capsule may be a hollow structure, such as a vessel, container, receptacle, or the like, which can be configured to hold the heart valve at least partially therein. The capsule may have multiple parts configured to move relative to each other so as to selectively retain and release the valve. For example, in some embodiments the capsule may include an atrial capsule portion and a ventricular capsule portion situated distal to the atrial capsule portion. The atrial and ventricular capsule portions may each be hollow structures and may be drawn together to form a receptacle in which the heart valve may be held. In some embodiments, the outer diameter of the atrial capsule portion may be equal to the outer diameter of the ventricular capsule portion. In some alternative embodiments, the outer diameter of the atrial capsule portion may be larger than or smaller than the outer diameter of the ventricular capsule portion. In some embodiments, the capsule may be positioned distal to the distal ends of the first and second catheters. The capsule may be configured to retain a heart valve therein and to deliver the heart valve through the anatomy (e.g., vasculature) to the heart valve implantation site. That is, the capsule may be configured to retain the heart valve therein during transvascular advancement of the capsule. In some embodiments, the capsule may be configured to retain the heart valve in a radially-contracted configuration, such that the heart valve may easily pass through the anatomy during delivery to the implantation site. In some embodiments, the capsule may be constructed from a variety of suitable, biocompatible materials, some non-limiting examples including plastics, metals, silicone, Pebax, rubber, nylon, polyurethane, polyethylene terephthalate (PET), latex, thermoplastic elastomers, silicone, and polyimides. Additionally, or alternatively, the exemplary capsule may include one or more radiopaque markers and/or a radiopaque coating, such that the capsule location may be tracked during advancement of the capsule through the body.

In the example depicted in FIG. 7B, an exemplary capsule 7300 may be situated at the distal end of the implant catheter 8100 (i.e., the exemplary first catheter). Capsule 7300 may include multiple capsule portions, including proximal capsule portion 7320 (which may constitute an atrial capsule portion), distal capsule portion 7340 (which may constitute a ventricular capsule portion), and a nose cone 7360. As illustrated in FIG. 8C, an exemplary prosthetic heart valve 6000 may be held in a radially-contracted configuration within exemplary capsule 7300. For the sake of illustration, only heart valve frame 2000 of FIG. 2A is illustrated in FIG. 8C; however, one of ordinary skill will understand that the entirety of prosthetic valve 6000 may be held within capsule 7300 in the manner illustrated in FIG. 8C. In some embodiments, a portion of the capsule may be secured to the first catheter. For example, as illustrated in FIG. 7B, implant catheter 8100 (i.e., the exemplary first catheter) may be secured to distal capsule portion 7340 via torque shaft 8300, one end of which may be received at least partially within implant catheter 8100 and the other end of which may be directly connected to the distal capsule portion 7340.

In some embodiments, the heart valve delivery system may include an ejector associated with the capsule. The ejector may be configured to release the heart valve from within the capsule. In some embodiments, the ejector may be configured to move different portions of the capsule proximally and distally (relative to the first, second, and third catheters and relative to the heart valve) so as to release the heart valve from within the capsule. For example, the ejector may be connected to the different portions of the capsule and may be configured to effect longitudinal movement of the different capsule portions relative to the other portions of the exemplary heart valve delivery system. In some embodiments, the ejector may include one or more features situated at least partially inside the capsule and configured to drive movement of portions of the capsule relative to the heart valve. Additionally, or alternatively, the ejector may include one or more features situated outside of the capsule and configured to drive movement of portions of the capsule relative to the heart valve.

In the example illustrated in FIG. 7B, the ejector may include capsule shaft 7230 and torque shaft 8300. Capsule shaft 7230 may be connected (e.g., at connection 8400 shown in FIG. 8C) to the proximal capsule portion 7320 and may be configured for axial movement relative to implant catheter 8100 (i.e., the exemplary first catheter), guide catheter 7220 (i.e., the exemplary second catheter), and outer sheath 7210 (i.e., the exemplary third catheter). Accordingly, the proximal capsule portion 7320 may be configured for axial movement relative to the first, second, and third catheters via axial movement of the capsule shaft 7230. In some embodiments, the capsule shaft may be included within the telescoping catheter assembly and may be situated within the guide catheter 7220. The connection between the capsule shaft 7230 and the proximal capsule portion 7320 can be any connection mechanism such as a weld, an adhesive, an interference fit, threads, barbs, clamp(s), over-molding, magnetic connection, and other suitable mechanical or electromechanical connection mechanisms.

In the example illustrated in FIG. 7B, the ejector may additionally or alternatively include torque shaft 8300. As illustrated in FIG. 7B, the proximal end of torque shaft 8300 may be configured to be received within the distal end of implant catheter 8100 (for example, via a screw or threaded arrangement). The distal end of torque shaft 8300 may be connected to, or otherwise secured relative to, the distal capsule portion 7340. Torque shaft 8300 may be configured for longitudinal movement relative to implant catheter 8100 (e.g., by actuation of the threaded arrangement), thus causing longitudinal movement of the distal capsule portion 7340.

An exemplary heart valve delivery system may include a control handle assembly configured to control different components of the heart valve delivery system. For example, the control handle assembly may include one or more control mechanisms that may be actuated by a user to effect movement of different components of the heart valve delivery system, such as the first catheter, second catheter, third catheter, flexure radii, capsule, and/or ejector. In some embodiments, the control handle assembly may be configured to permit at least two of the first catheter, second catheter, and third catheter to rotate together. That is, the control handle assembly may be configured to cause synchronized rotation of at least two of the catheters. In some embodiments, the control handle assembly may be configured to cause rotation of all three of the catheters. For example, the control handle assembly may include any suitable control mechanism, including a knob, lever, rotatable cuff, slider, or any other structure capable of causing rotation of two or more catheters together. The control handle assembly may be connected to the two or more catheters (e.g., by welding, adhesive, interference fit, over molding, threading, barbs, or any other suitable connection mechanism) to as to control rotational movement of the two or more catheters. FIG. 7A illustrates an exemplary control handle assembly 7100 that may be configured to permit rotation (by actuation of outer sheath rotation knob 7182) of guide catheter 7220 and outer sheath 7210. Guide catheter 7220 and outer sheath 7210 may be configured to rotate together. In some embodiments, the exemplary control handle assembly may additionally be configured to rotate the first catheter. For example, implant catheter rotation knob 7186 illustrated in FIG. 7A may be configured to rotate implant catheter 8100 (i.e., the exemplary first catheter) about its longitudinal axis. Although control handle assembly 7100 is depicted in FIG. 7A as including knobs 7182 and 7186 to control catheter rotation, one of ordinary skill will understand that the exemplary control handle assembly may include any suitable mechanism for controlling catheter rotation, such as a wheel, a slider, a lever, a joystick, a touchpad, a rotatable cuff, or any other structure configured to control catheter rotation.

Additionally, or alternatively, the exemplary control handle assembly may be configured to independently adjust the first and second flexure radii. For example, the control handle assembly may include a second catheter steering mechanism that may be configured to control bending of the first flexure radius of the second catheter, and the control handle assembly may also include a third catheter steering mechanism that may be configured to control bending of the second flexure radius of the third catheter. The second catheter steering mechanism and third catheter steering mechanism may be actuated individually such that the first and second flexure radii may be adjusted individually. The control handle assembly may include any appropriate steering mechanisms, examples of which include, but are not limited to, a rotatable knob, a wheel, a joystick, a touchpad, and combinations thereof, among other steering mechanisms capable of effecting bending of the second and third catheters at the first and second flexure radii. Feature(s) of the control handle assembly configured to adjust the flexure radii (e.g., a second catheter steering mechanism and a third catheter steering mechanism) may have similar or the same structure or could take different forms. In some embodiments, the second catheter steering mechanism and third catheter steering mechanism may be independently actuated by a user to effect bending of the first flexure radius of the second catheter and the second flexure radius of the third catheter. For example, exemplary control handle assembly 7100 depicted in FIG. 7A may include a guide catheter steering knob 7142 configured to bend guide catheter 7220 (i.e., the exemplary second catheter of delivery system 7000) and an outer sheath steering knob 7122 configured to bend outer sheath 7210 (i.e., the exemplary third catheter of delivery system 7000). Knobs 7122 and 7142 may be actuated independently, without actuation of the other knob, or knobs 7122 and 7142 may be actuated simultaneously. Accordingly, guide catheter steering knob 7142 may be considered a second catheter steering mechanism and outer sheath steering knob 7122 may be considered a third catheter steering mechanism of delivery system 7000 in some embodiments. Although actuators 7120 and 7140 are depicted in FIG. 7A as including knobs 7122 and 7142, respectively, to control catheter bending (i.e., to adjust the flexure radii), one of ordinary skill will understand that the exemplary control handle assembly may include any suitable mechanism for controlling catheter bending, such as a wheel, a slider, a lever, a joystick, a touchpad, a rotatable cuff, or any other structure configured to control catheter bending.

Additionally, or alternatively, the exemplary control handle assembly may be configured to cause relative axial movement between the first catheter, the second catheter, and the third catheter. For example, the control handle assembly may include one or more control handle portions that may be connected to the first catheter, the second catheter, and the third catheter (e.g., by welding, adhesive, interference fit, over molding, threading, barbs, or any other suitable connection mechanism), and may be configured to cause relative longitudinal movement between them. The control handle portions may be configured to move longitudinally relative to each other (e.g., on a slider, a rod, a rail, a track, or any suitable guide structure) to control relative axial movement between the catheters. For example, axial movement of the control handle portions may be controlled by rotatable knobs, wheels, joysticks, touchpads, sliders, or any other suitable mechanism for controlling axial movement.

In the example illustrated in FIG. 7A, exemplary control handle assembly 7100 may include an outer sheath control handle 7120, guide catheter control handle 7140, and implant catheter control handle 7160, which may be connected to the outer sheath 7210, the guide catheter 7220, and the implant catheter 8100, respectively. In some embodiments, the outer sheath control handle 7120 and guide catheter control handle 7140 may be mounted upon a cradle 7180, to which the outer sheath control handle 7120 may be secured. Cradle 7180 may include a toothed gear configured to be rotated by rotation knob 7188. Guide catheter control handle 7140 may include a toothed rack configured to engage the toothed gear. In some embodiments, rotation of the toothed gear due to rotation of knob 7188 may cause guide catheter control handle 7140 to translate longitudinally relative to the cradle 7180 and to the outer sheath control handle 7120 due to engagement of the toothed rack with the rotating toothed gear. This movement of guide catheter control handle 7140 may move the guide catheter 7220 relative to the outer sheath 7210 and implant catheter 8100. Additionally, or alternatively, implant catheter control handle 7160 may be configured to axially translate relative to the control handle assembly, such as within track 7420 of stand 7400. Translation of the implant catheter control handle 7160 may cause longitudinal movement of implant catheter 8100 relative to the outer sheath 7210 and the guide catheter 7220. Although delivery system 7000 is depicted in FIG. 7A as including a gear and rack assembly to control movement between cradle 7180 and guide catheter control handle 7140, one of ordinary skill will understand that the exemplary heart valve delivery system may include any suitable mechanism for controlling movement between cradle 7180 and guide catheter control handle 7140, such as a threaded arrangement, a locking slider, a worm drive arrangement, or a belt drive. For example, a worm drive arrangement may be included within delivery system 7000 to control movement between cradle 7180 and guide catheter control handle 7140. Advantageously, the worm drive arrangement may allow continuous linear movement between the cradle 7180 and the guide catheter control handle 7140, while also enabling the cradle 7180 and guide catheter control handle 7140 to remain fixed relative to each other, regardless of the particular position of the guide catheter control handle 7140 relative to the cradle.

Additionally, or alternatively, the exemplary control handle assembly may be configured to permit the ejector to cause relative movement between the heart valve and the capsule. For example, the control handle assembly may be configured to control movement of the ejector, and thus, may be configured to control movement of the different portions of the capsule, such as atrial and ventricular capsule portions, to release the heart valve from the capsule. The control handle assembly may have a first component configured to control component of the ejector that moves the ventricular capsule portion, and the control handle assembly may have a second component configured to control the component of the ejector that moves the atrial capsule portion. The first and second components of the control handle assembly may be mechanisms such as a rotatable knob, a slider, a wheel, a lever, a rotatable cuff, a slider, or any other suitable structure configured to control the components of the ejector.

For example, FIG. 7A shows exemplary control handle assembly 7100 including a proximal capsule portion slider 7162 and a distal capsule portion knob 7170. Proximal capsule portion slider 7162 may be configured to control axial movement of the capsule shaft 7230 (e.g., due to a physical connection therebetween) such that proximal capsule portion slider 7162 may be configured to control axial movement of the proximal capsule portion 7320. The distal capsule portion knob 7170 may be configured to control axial movement of the distal capsule portion 7340. For example, distal capsule portion knob 7170 may be configured to control longitudinal movement of torque shaft 8300 (illustrated in FIG. 7B) relative to implant catheter 8100 and valve anchor disc 8200. Accordingly, rotation of distal capsule portion knob 7170 may cause axial movement of the distal capsule portion 7340. Although control handle assembly 7100 is depicted in FIG. 7A as including proximal capsule portion slider 7162 and distal capsule portion knob 7170 to control ejector movement, one of ordinary skill will understand that the exemplary control handle assembly may include any suitable mechanism for controlling ejector movement, such as a wheel, a slider, a lever, a joystick, a touchpad, or a rotatable cuff.

In some embodiments, the capsule may include one or both of an atrial capsule portion and a ventricular capsule portion, which may be configured for relative longitudinal movement. The ventricular capsule portion may refer to a portion of the capsule configured to contain the ventricular end of the heart valve; the ventricular capsule portion may correspond with the distal end of the capsule. Similarly, the atrial capsule portion may refer to a portion of the capsule configured to contain the atrial end of the heart valve; the atrial capsule portion may correspond with the proximal end of the capsule. The atrial and ventricular capsule portions may be configured for axial movement away from and towards the other. For example, FIGS. 8A-8C show an exemplary capsule 7300, with a ventricular capsule portion (e.g., distal capsule portion 7340) and an atrial capsule portion (e.g., proximal capsule portion 7320). FIG. 8A shows the capsule portions 7320, 7340 drawn together such that the capsule may be configured in a closed position. In the closed position, the capsule may be devoid of openings into the capsule interior and may optionally be airtight. FIG. 8B illustrates an example of the capsule 7300 with distal capsule portion 7340 (i.e., the exemplary ventricular capsule portion) and proximal capsule portion 7320 (i.e., the exemplary atrial capsule portion) positioned apart such that the capsule may be configured in an open position, in which distal capsule portion 7340 may be positioned apart from proximal capsule portion 7320. In some embodiments, distal capsule portion 7340 may be configured for longitudinal movement relative to the proximal capsule portion 7320 via actuation of distal capsule portion knob 7170. Additionally, or alternatively, proximal capsule portion 7320 may be configured for longitudinal movement relative to the distal capsule portion 7340 via actuation of proximal capsule portion slider 7162.

In some embodiments, the ventricular capsule portion may be configured to retain an annular valve body of the heart valve within the ventricular capsule portion. The annular valve body may be a ring-shaped structure of the heart valve having at least one opening within the annular valve body. The at least one opening may extend longitudinally along the entire length of the annular valve body. For example, annular valve body 2020 illustrated in FIG. 2B may include an axial lumen 2022 extending longitudinally through the annular valve body. In some embodiments, the annular valve body may be sized and configured to be seated within the orifice of a native valve when the heart valve is implanted in the orifice of the native valve, and may include a flow control device, such as one or more leaflets, within the opening of the annular valve body. In some embodiments, the entire annular valve body may be retained within the ventricular capsule portion. Alternatively, a portion of the annular valve body may be retained within the ventricular capsule portion. In the example depicted in FIG. 8C, prosthetic heart valve 6000 may include annular valve body 2020, the entire length of which may be retained within the distal capsule portion 7340 (that is, the ventricular capsule portion).

Additionally, or alternatively, the ventricular capsule portion may be configured to retain ventricular anchoring legs of the heart valve within the ventricular capsule portion. In some embodiments, the ventricular anchoring legs may be configured to engage ventricular tissue of a native atrioventricular valve (e.g., a mitral valve) to anchor the heart valve within the native atrioventricular valve. For example, FIGS. 10F-10H depict ventricular anchoring legs 2240 situated within ventricle 9020 and engaging the ventricular side of native mitral valve 9030, so as to anchor prosthetic heart valve 6000 within the mitral valve 9030. In some embodiments, the ventricular anchoring legs may extend from or otherwise be connected to the annular valve body of the heart valve. In some embodiments, some or all of the ventricular anchoring legs may be entirely retained within the ventricular capsule portion. Alternatively, one or more ventricular anchoring legs may be so configured such that a portion of the one or more ventricular anchoring legs is retained outside of the ventricular capsule portion (e.g., within another portion of the capsule). In the example depicted in FIG. 8C, prosthetic heart valve 6000 may include a plurality of ventricular anchoring legs 2240, each of which may be entirely retained within the distal capsule portion 7340 (i.e., the exemplary ventricular capsule portion).

In some embodiments, the atrial capsule portion may be configured to retain a plurality of atrial anchoring arms of the heart valve within the atrial capsule portion. Exemplary atrial anchoring arms may be configured to engage atrial tissue of a native atrioventricular valve (e.g., a mitral valve) to anchor the heart valve within the native atrioventricular valve. For example, FIG. 10F-10H depict atrial anchoring arms 2440 situated within atrium 9010 and engaging the atrial side of native mitral valve 9030, so as to anchor prosthetic heart valve 6000 within the mitral valve. In some embodiments, the atrial anchoring arms may extend from or otherwise be connected to the annular valve body of the heart valve. In some embodiments, some or all of the atrial anchoring arms may be entirely retained within the atrial capsule portion. Alternatively, one or more atrial anchoring arms may be so configured such that a portion of the one or more atrial anchoring arms is retained within the atrial capsule portion. In the example depicted in FIG. 8C, prosthetic heart valve 6000 may include a plurality of atrial anchoring arms 2440. As shown in FIG. 8C, a portion of each exemplary atrial anchoring arm 2440 may be retained within the atrial capsule portion 7320, including the distal arm ends 2444, while the remainder may be retained within the ventricular capsule portion 7340, including connection locations 2202.

In some embodiments, the capsule may include a valve anchor configured to engage the annular valve body of the heart valve. The valve anchor may be located within the capsule (e.g., within the ventricular capsule portion) and may selectively prevent longitudinal movement of the heart valve relative to the capsule. In some embodiments, the valve anchor may directly engage the heart valve to secure the heart valve against longitudinal movement. For example, the valve anchor may include one or more recesses positioned around its circumference that may be configured to receive and retain a portion of the heart valve. The recesses in the valve anchor may include slots, holes, hooks, openings, or any suitable receptacle configured to receive at least a portion of the heart valve, such as one or more ventricular end delivery posts. For example, FIG. 8C illustrates valve anchor disc 8200, which is secured to the distal end of implant catheter 8100 and which includes anchor disc recesses 8205 about its circumference. Recesses 8205 are configured to receive ventricular end delivery posts 2028 of the heart valve, thus securing the heart valve 6000 within the capsule in the arrangement illustrated in FIG. 8C. The ventricular end delivery posts 2028 may be positioned on or near the ventricular end 2025 of the annular valve body 2020 and may take a number of forms and shapes including D-shaped, tapered, threaded, barbed, or keyed, among others. In some embodiments, the recesses may secure the heart valve against axial movement until the annular valve body 2020 expands completely, causing the ventricular end delivery posts 2028 to translate or slide out of recesses 8205, thus releasing the heart valve from the valve anchor.

In some embodiments, the ejector may be configured to release the annular valve body from engagement with the valve anchor and from retention within the capsule. As discussed above, the annular valve body may be constrained within, and thus prevented from axially expanding by, the ventricular capsule portion. The ejector may include a portion thereof configured to axially move the ventricular capsule portion relative to the rest of the capsule (for example, torque shaft 8300, which may be controlled by distal capsule portion knob 7170). The ejector (specifically, torque shaft 8300) may release the annular valve body 2020 from the valve anchor disc 8200 by moving the ventricular capsule portion 7340 in the distal direction relative to implant catheter 8100 and valve anchor disc 8200 until the entire annular valve body 2020 is free from constraining force exerted on it by the ventricular capsule portion 7340. The annular valve body 2020 may radially expand due to its shape memory properties, thus releasing the ventricular end delivery posts 2028 from engagement with the valve anchor recesses 8205.

In some embodiments, the ejector may be configured to effect movement between the capsule and the plurality of ventricular anchoring legs while the annular valve body remains engaged with the valve anchor. In some embodiments, the annular valve body and ventricular anchoring legs may be received and constrained within the ventricular capsule portion, with the annular valve body portioned distal to (i.e., in a ventricular direction from) the ventricular anchoring legs. FIG. 8C illustrates an example in which annular valve body 2020 and ventricular anchoring legs 2240 may be received in and constrained within ventricular capsule portion 7340. As described above, the ejector (e.g., torque shaft 8300) may be configured to move the ventricular capsule portion in a longitudinal direction. In some embodiments, the ejector may be configured to move the ventricular capsule portion to a position in which the terminal ends of the legs are no longer retained within the ventricular capsule portion, but in which the annular valve body remains retained within the ventricular capsule portion. As the ventricular anchoring legs emerge from the ventricular capsule portion, the ventricular anchoring legs may be free from radially-constraining forces and may deflect radially outward (e.g., due to their shape-memory properties). However, at least a portion of the annular valve body remains retained within the ventricular capsule portion at this position of the ventricular capsule portion. Accordingly, the annular valve body may remain radially-constrained by the ventricular capsule portion and may be prevented from radially expanding. As a result, the annular valve body may remain engaged with and secured against axial movement by the valve anchor. FIG. 10E illustrates an example of such a position of the ventricular capsule portion 7340, in which portions of ventricular anchoring legs 2240 deflect radially outward and in which annular valve body 2020 remains radially constrained.

The ejector may be configured to further move the ventricular capsule portion in the ventricular, distal direction until the annular valve body is no longer contained within the ventricular capsule portion. At such a point, the annular valve body may be free from radially-constraining forces and may expand radially outward (e.g., due to its shape-memory properties). As a result, the annular valve body may be freed from engagement with the valve anchor (e.g., due to radial movement of ventricular end delivery posts 2028 out of the recesses 8205 of the valve anchor disc 8200). FIG. 10G illustrates an example of such a position of the ventricular capsule portion 7340, in which the annular valve body 2020 is permitted to radially expand.

In some embodiments, an axial length of the ventricular capsule portion may be at least twice as long as an axial length of the atrial capsule portion. In some embodiments, the axial length of the ventricular capsule portion may include the axial length of a flexible protective feature secured to the distal end of the ventricular capsule portion (such as nose cone 7360 illustrated in FIG. 7B). In some alternative embodiments, the axial length of the ventricular capsule portion may refer to the axial length of the portions of the ventricular capsule portion which form the receptacle configured to retain the prosthetic valve; in such embodiments, the axial length of a flexible, protective feature, such as nose cone 7360, does not contribute to the axial length of the ventricular capsule portion. In some embodiments, the ventricular capsule portion may have an axial length of between 35 mm and 60 mm. In some embodiments, the ventricular capsule portion may have an axial length of between 38 mm and 42 mm. For example, and without limitation, the ventricular capsule portion may have an axial length of 38 mm, 39 mm, 40 mm, 41 mm, 42 mm, or any other suitable axial length. In such embodiments, the axial length of the ventricular capsule portion may not include the axial length of a flexible, distal feature (such as a nose cone 7360). In some alternative embodiments, the ventricular capsule portion may have an axial length of between 50 and 55 mm. For example, and without limitation, the ventricular capsule portion may have an axial length of 50 mm, 51 mm, 52 mm, 52.5 mm, 53 mm, 53.1 mm, 53.2 mm, 53.3 mm, 53.4 mm, 53.5 mm, 53.6 mm, 53.7 mm, 53.8 mm, 53.9 mm, 54 mm, 54.5 mm, 55 mm, or any other suitable axial length. In such embodiments, the axial length of the ventricular capsule portion may include the entire axial length of the ventricular capsule portion, including any flexible distal features secured to the ventricular capsule portion (such as a nose cone 7360). In some embodiments, the atrial capsule portion may have an axial length between 12 mm and 20 mm. For example, and without limitation, the atrial capsule portion may have an axial length of 12 mm, 13 mm, 14 mm, 14.5 mm, 15 mm, 15.5 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.5 mm, 18 mm, 19 mm, 20 mm, or any other suitable axial length. For example, in FIGS. 8A-8C, an axial length of capsule 7300 or a portion of capsule 7300 may be a length along an axis extending from left to right. In some embodiments, the axial length of the ventricular capsule portion may extend from a proximal end of the ventricular capsule portion (e.g., the right side of distal capsule portion 7340 in FIGS. 8A and 8B) to a distal end of the ventricular capsule portion (e.g., the intersection between distal capsule portion 7340 and nose cone 7360 in FIGS. 8A and 8B). The axial length of the atrial capsule portion may extend between the proximal and distal ends of the atrial capsule portion.

In some embodiments, the control handle assembly may be configured to assume a capsule lock configuration in which the ejector may be prevented from moving the ventricular capsule portion beyond a pre-determined location. Specifically, in the capsule lock configuration, the ejector may be prevented from moving the ventricular capsule portion in a ventricular, distal direction beyond the pre-determined location. In some embodiments, when the control handle assembly is in the capsule lock configuration, the portion of the control handle assembly configured to control movement of the ventricular capsule portion may be prevented from moving beyond a predetermined axial and/or rotational position associated with placement of the ventricular capsule portion at the pre-determined location. In the example depicted in FIG. 7A, when control handle assembly 7100 is in the capsule lock configuration, knob 7170 may be prevented from rotation beyond the rotational position that arranges distal capsule portion 7340 at the pre-determined location. In some embodiments, the control handle assembly may assume the capsule lock configuration via actuation of a capsule lock mechanism, which may be incorporated within the control handle assembly. The capsule lock mechanism may include any suitable manual control mechanism, including a button, knob, lever, tab, rotatable cuff, slider, or any other structure configured to prevent movement of the ventricular capsule portion beyond the predetermined location. For example, FIG. 7A shows distal capsule portion knob lock 7172 that may prevent rotation of knob 7170 beyond a certain rotational position.

In some embodiments, the pre-determined location of the ventricular capsule portion may correspond to a position of the ventricular capsule portion in which the ventricular anchoring legs may be released from the ventricular capsule portion and in which the annular valve body may remain constrained within the ventricular capsule portion (e.g., the arrangement depicted in FIG. 5B or FIG. 5D). Advantageously, the capsule lock configuration may prevent the inadvertent release of the annular valve body due to incorrect positioning of the ventricular capsule portion. In some embodiments, the control handle assembly may be held in the capsule lock configuration during advancement of the capsule through the body to the heart valve implantation site, so as to prevent inadvertent expansion and release of the heart valve during delivery. In some embodiments, the heart valve can assume the positions shown in FIG. 10A-10F in the capsule lock configuration but may be prevented from moving into the fully-expanded configuration shown in FIGS. 10G and 10H as long as the handle stays in the capsule lock configuration. In some embodiments, the capsule lock configuration may not limit movement of the atrial capsule portion by the ejector. For example, the heart valve can assume the configurations shown in FIGS. 5C, 5D, and 10F when the handle is still in the capsule lock configuration.

In some embodiments, the control handle assembly may also be configured to assume a capsule release configuration in which the ejector is permitted to move the ventricular capsule portion beyond the pre-determined location. For example, in the capsule release configuration, the ejector may move the ventricular capsule portion in the ventricular, distal direction beyond the pre-determined location. In some embodiments, when the control handle assembly is in the capsule release configuration, the portion of the control handle assembly configured to control movement of the ventricular capsule portion by the ejector may be configured to move beyond the axial and/or rotational position thereof which is associated with the pre-determined location of the ventricular capsule portion. In the example depicted in FIG. 7A, when control handle assembly 7100 is in the capsule release configuration, knob 7170 may be configured for rotation beyond the associated with the positioning of the distal capsule portion 7340 (i.e., the exemplary ventricular capsule portion) at the pre-determined location. In some embodiments, the control handle assembly may assume the capsule release configuration via release or deactivation of the capsule lock mechanism. Upon the control handle assembly assuming the capsule release configuration, the ejector may be configured to move the ventricular capsule portion in the ventricular, distal direction up to and beyond the pre-determined location. In some embodiments, advancement of the ventricular capsule portion beyond the pre-determined location may move the ventricular capsule portion beyond the ventricular, distal end of the annular valve body of the heart valve. As a result, annular valve body may be released from the ventricular capsule portion and allowed to radially expand (for example, as illustrated in FIG. 5E), thus freeing the annular valve body from engagement with the valve anchor. During the exemplary implantation procedure illustrated in FIGS. 10A-10H, prosthetic heart valve 6000 may be prevented from assuming the fully-expanded configuration depicted in FIGS. 10G and 10H until the control handle assembly assumes the capsule release configuration. Upon assumption of the capsule release configuration, the prosthetic heart valve 6000 may assume the fully-expanded configuration depicted in FIGS. 10G and 10H and may be anchored at the implantation site (e.g., within mitral valve 9030).

FIG. 7A shows an exemplary ventricular capsule lock mechanism (e.g., distal capsule portion knob lock 7172) configured, when engaged, to prevent the ejector from advancing the ventricular capsule portion beyond the pre-determined location. The distal capsule portion knob lock 7172 may be a tab or button that a user may selectively engage or disengage by pushing or pulling on the distal capsule portion knob lock 7172. In some embodiments, when the distal capsule portion knob lock 7172 is engaged, rotation of distal capsule portion knob 7170 may be prevented beyond a certain rotational position, thereby preventing movement of the ventricular capsule portion, by the ejector, beyond the pre-determined location. In alternative embodiments, engagement of distal capsule portion knob lock 7172 may secure torque shaft 8300 within, or relative to, capsule interior rod 8100, thus preventing ventricular, distal movement of torque shaft 8300 and distal capsule portion 7430. Accordingly, expansion of the annular valve body, and thus the final release of the heart valve, may be prevented.

In some embodiments, the ejector may be situated at least partially within the first catheter. For example, a portion of the ejector may be configured to be positioned at least partially within the first catheter and may be configured for axial movement relative to the catheter. For example, FIGS. 7B and 8C show an exemplary torque shaft 8300, which may form part of the ejector. Implant catheter 8100 (i.e., the exemplary first catheter) is configured to receive torque shaft 8300. Implant catheter 8100 and torque shaft 8300 may also be configured for relative longitudinal movement. For example, an external surface of torque shaft 8300 may include threading configured to engage threading on an interior surface of the distal end of implant catheter 8100. Alternatively, other mechanisms may be employed to control axial movement between implant catheter 8100 and torque shaft 8300.

In some embodiments, the control handle assembly may include a guide actuator configured to effect movement of the second catheter. Additionally, or alternatively, the control handle assembly may include a sheath actuator configured to effect movement of the third catheter. In some embodiments, an "actuator" may be a handle structure with one or more control mechanisms to effect movement of a catheter. For example, FIG. 7A illustrates exemplary prosthetic valve delivery system 7000, which may include an outer sheath control handle 7120 and a guide catheter control handle 7140. Outer sheath control handle 7120 may be configured to effect bending of outer sheath 7210 (i.e., the exemplary third catheter) via outer sheath steering knob 7122. Accordingly, outer sheath control handle 7120 may be considered a sheath actuator. Similarly, guide catheter control handle 7140 may be configured to effect bending of guide catheter 7220 (i.e., the exemplary second catheter) via guide catheter steering knob 7124. Accordingly, guide catheter control handle 7140 may be considered a guide actuator.

In some embodiments, one or both of the guide actuator and sheath actuator may be configured to effect proximal and distal movement of the second and third catheters, respectively. For example, guide catheter control handle 7140 (i.e., the exemplary guide actuator) may be configured to move the second catheter proximally and distally via engagement with rotating knob 7188. Additionally, or alternatively, one or both of the guide actuator and sheath actuator may be configured to effect bending of the second and third catheters, respectively. For example, outer sheath control handle 7120 (i.e., the exemplary sheath actuator) and guide catheter control handle 7140 may be connected to, or otherwise associated with, one or more pull wires connected to and configured to cause bending of the third catheter and the second catheter, respectively. In some embodiments, the pull wires may be operably connected with steering knobs 7142 and 7122 to control bending of the first and second adjustable flexure radii, respectively. In some embodiments, the sheath actuator and the guide actuator may include other mechanisms suitable for effecting catheter bending.

In some embodiments, outer sheath control handle 7120 (i.e., the exemplary sheath actuator) and guide catheter control handle 7140 (i.e., the exemplary guide actuator) may be mounted upon a cradle 7180, which may in turn be secured to a stand 7400. For example, cradle 7180 may be locked to stand 7400 and may be configured to be released therefrom by actuation of release button 7184. In some embodiments, outer sheath control handle 7120 may be secured to cradle 7180 (for example, in a separable manner) such that relative longitudinal movement between handle 7120 and cradle 7180 is prevented. In addition, and as discussed above, guide catheter control handle 7140 may be configured to move longitudinally relative to cradle 7180 due to rotation of knob 7188. In some embodiments, cradle 7180 may include an outer sheath rotation knob 7182 configured to engage and rotate outer sheath 7210 (i.e., the exemplary third catheter) and guide catheter 7220 (i.e., the exemplary second catheter) about their respective longitudinal axes. In some embodiments, outer sheath rotation knob 7182 may also rotate implant catheter 8100 (i.e., the exemplary first catheter) about its longitudinal axis. In alternative embodiments, implant catheter 8100 may be secured against rotation caused by rotation knob 7182 and may instead be rotated about its longitudinal axis by rotation knob 7186, which may also be included within cradle 7180.

In some embodiments, the control handle assembly may include a capsule handle configured to control the various components of the ejector. For example, the capsule handle may be secured to, or otherwise operably connected to, the various components of the ejector such that the control handle assembly may be configured to control longitudinal movement of the ventricular and atrial capsule portions via the ejector. The capsule handle may include any suitable control mechanism for controlling the various components of the ejector. For example, FIG. 7A illustrates exemplary prosthetic valve delivery system 7000, which may include an implant catheter control handle 7160. Implant catheter control handle 7160 may include proximal capsule portion slider 7162, which may be configured to control movement of capsule shaft 7230 and of proximal capsule portion 7320. Implant catheter control handle 7160 may additionally or alternatively include distal capsule portion knob 7170, which may be configured to control movement of torque shaft 8300 and distal capsule portion 7340. Accordingly, implant catheter control handle 7160 may be considered a capsule handle. In some embodiments, the capsule handle may be connected to, or otherwise secured relative to, the first catheter. As a result, movement of the capsule handle may control axial movement of the first catheter. For example, implant catheter control handle 7160 (i.e., the exemplary capsule handle) may be connected to, and configured to control axial movement of, implant catheter 8100 (i.e., the exemplary first catheter).

In some embodiments, the guide actuator, the sheath actuator, and the capsule handle may be configured for longitudinal movement relative to each other. For example, at least two of the guide actuator, sheath actuator, and capsule handle may be configured for longitudinal movement relative to the control handle assembly. In some embodiments, the control handle assembly may include elements configured to guide longitudinal movement of the guide actuator, sheath actuator, and/or capsule handle, such as a slider, a rod, a rail, a track, or any other suitable structure. In the example illustrated in FIG. 7A, the guide catheter control handle 7140 (i.e., the exemplary guide actuator) may be configured for longitudinal movement relative to the outer sheath control handle 7120 (i.e., the exemplary sheath actuator) and the implant catheter control handle 7160 (i.e., the exemplary capsule handle) due to rotation of knob 7188. Additionally or alternatively, the implant catheter control handle 7160 may be configured for longitudinal movement relative to the outer sheath control handle 7120 and guide catheter control handle 7140 by sliding along track 7420 of stand 7400.

In some embodiments, the capsule handle may include a first release actuator configured to control relative movement between a first portion of the capsule and the heart valve, while the heart valve remains longitudinally fixed relative to the first catheter. In some embodiments, the first portion of the capsule may include the atrial capsule portion. For example, the first release actuator may be configured to effect longitudinal movement of the atrial capsule portion relative to the heart valve, which may be secured against longitudinal movement relative to the first catheter due to the heart valve's engagement with the valve anchor. For example, in FIG. 7A, implant catheter control handle 7160 (i.e., the exemplary capsule handle) may include a proximal capsule portion slider 7162 configured to control relative movement between the proximal capsule portion 7320 and a heart valve anchored by valve anchor disc 8200. Accordingly, proximal capsule portion slider 7162 may be considered a first release actuator in some embodiments. In some embodiments, the heart valve may remain longitudinally fixed relative to the first catheter during use of the first release actuator because the first release actuator is not configured to control movement of portions of the capsule configured to release the valve from the valve anchor. For example, proximal capsule portion slider 7162 may be configured to control movement of the proximal capsule portion 7320, while the distal capsule portion 7340 may be configured to control release of the valve 6000 from the valve anchor disc 8200.

In some embodiments, the capsule handle may additionally or alternatively include a second release actuator configured to control release of the heart valve from the capsule by the ejector. For example, the second release actuator may be configured to control the portion of the ejector that, in turn, is configured to control movement of the ventricular capsule portion. For example, in FIG. 7A, implant catheter control handle 7160 (i.e., the exemplary capsule handle) may include a distal capsule portion knob 7170 configured to control longitudinal movement of torque shaft 8300 and distal capsule portion 7340. Accordingly, distal capsule portion knob 7170 may be considered a second release actuator in some embodiments. In some embodiments, and as discussed above, the ventricular capsule portion 7340 may be configured to radially constrain the annular valve body 2020, while the ventricular end delivery posts 2028 of the heart valve 6000 are positioned within anchor recesses 8205 (as illustrated in FIG. 8C). Distal capsule portion knob 7170 (i.e., the second release actuator) may be configured to control release of the heart valve 6000 by moving the ventricular capsule portion 7340 distally until the annular valve body 2020 is removed from the ventricular capsule portion and allowed to radially expand. Radial expansion of the annular valve body 2020 may cause the ventricular end delivery posts 2028 to translate or slide out of the anchor recesses 8205, thus releasing the heart valve 6000 from the valve anchor disc 8200 and from the capsule 7300.

In some embodiments, the capsule handle may be configured to assume an anchoring configuration in which the second release actuator is prevented from controlling the ejector to release the heart valve from the capsule. For example, in the anchoring configuration, the second release actuator may be prevented from moving the ejector and, by extension, the ventricular capsule portion beyond a pre-determined location in which the annular valve body of the heart valve is released from the ventricular capsule portion. In some embodiments, the second release actuator may be configured to control relative movement between a second portion of the capsule and the heart valve while the capsule handle is in the anchoring configuration. That is, when the capsule handle is in in the anchoring configuration, the second release actuator may be configured to effect ventricular, distal movement of the ejector and, by extension, the ventricular capsule portion (which may constitute the second portion of the capsule) relative to the heart valve to the pre-determined location, beyond which further distal movement of the ventricular capsule portion may be prevented. In the example depicted in FIG. 7A, the anchoring configuration of implant catheter control handle 7160 (i.e., the exemplary capsule handle) may correspond to a configuration in which distal capsule portion knob lock 7172 is activated, thus preventing distal capsule portion knob 7170 from moving torque shaft 8300 and distal capsule portion 7340 to a position at which the annular valve body 2020 is released from the distal capsule portion 7340.

In some embodiments, the capsule handle may additionally or alternatively be configured to assume a final release configuration in which the second release actuator is permitted to control the ejector to release the heart valve from the capsule. For example, in the final release configuration, the second release actuator may be configured to control the ejector to freely move the ventricular capsule portion distally and proximally, including to a position of the ventricular capsule portion in which the annular valve body, and thus the heart valve, are released from the valve anchor and from the capsule. In some embodiments, when the capsule handle is in the final release configuration, the second release actuator may be configured to assume positions which the second release actuator was prevented from assuming when the capsule handle was in the anchoring configuration. In the example depicted in FIG. 7A, the final release configuration of implant catheter control handle 7160 may correspond to a configuration in which distal capsule portion knob lock 7172 is deactivated, allowing the distal capsule portion knob 7170 to freely move torque shaft 8300 and distal capsule portion 7340 proximally and distally, including to a position at which the annular valve body 2020 is released from the distal capsule portion 7340. At such a position, the annular valve body 2020 may expand, thus freeing prosthetic heart valve 6000 from engagement with valve anchor disc 8200 and from capsule 7300.

In some embodiments, the capsule handle may include a slide lock configured to assume a locked position in which longitudinal movement of the first catheter may be prevented and an unlocked position in which the first catheter may be configured to move proximally and distally. For example, in FIG. 7A, implant catheter control handle 7160 may be configured to slide longitudinally within track 7420 of stand 7400. Because implant catheter 8100 (i.e., the exemplary first catheter) is connected to, or otherwise secured relative to, the implant catheter control handle 7160, longitudinal movement of handle 7160 may control longitudinal movement of implant catheter 8100. Implant catheter control handle 7160 may include a slide lock 7166, which may be configured to assume a locked position in which the slide lock 7166 fixes handle 7160 to its current position within track 7420. Locking of the implant catheter control handle 7160 via slide lock 7166 may prevent handle 7160 and implant catheter 8100 against longitudinal movement; accordingly, the slide lock 7166 may be considered the exemplary slide lock. Slide lock 7166 may also assume an unlocked position, in which implant catheter control handle 7160 may slide freely within track 7420. Although delivery system 7000 is depicted in FIG. 7A as including a locking slide arrangement to control movement between stand 7400 and implant catheter control handle 7160, one of ordinary skill will understand that the exemplary heart valve delivery system may additionally, or alternatively, include any suitable mechanism for controlling movement between stand 7400 and implant catheter control handle 7160, such as a rotatable lock, a gear and rack assembly, a threaded arrangement, or a belt drive.

In some embodiments, at least a portion of the capsule may be configured for longitudinal movement relative to the first catheter when the slide lock is in the locked position. For example, one or both of the atrial and ventricular capsule portions may be configured for longitudinal movement relative to the first catheter when the slide lock is in the locked position. In some embodiments, the first and second release actuators may be configured to effect longitudinal movement of the atrial and ventricular capsule portions, even when the capsule handle is secured against longitudinal movement by the slide lock. For example, in FIG. 7A, while implant catheter control handle 7160 (i.e., the exemplary capsule handle) is secured against longitudinal movement by slide lock 7166, proximal capsule portion slider 7162 (i.e., the exemplary first release actuator) may still be configured to control longitudinal movement of capsule shaft 7230 and proximal capsule portion 7320. The longitudinal movement of the proximal capsule portion 7320 may be relative to implant catheter 8100 (i.e., the exemplary first catheter), which may be connected to, or otherwise secured relative to, the implant catheter control handle 7160. Similarly, distal capsule portion knob 7170 (i.e., the second release actuator) may still be configured to control longitudinal movement of torque shaft 8300 and distal capsule portion 7340 relative to implant catheter 8100 while slide lock 7166 is in the locked position.

In some embodiments, the control handle assembly may be configured to prevent relative longitudinal movement between the first catheter and the second catheter. In some embodiments, for example, the control handle assembly may be configured to prevent relative longitudinal movement between the first catheter, the second catheter, and the third catheter. For example, the control handle assembly may be configured to secure the sheath actuator, the guide actuator, and the capsule handle against longitudinal movement, thus securing the first, second, and third catheters against longitudinal movement. The catheters and/or their corresponding control handles may be secured against longitudinal movement by any suitable mechanism, such as a knob, clip, lever, tab, rotatable cuff, slider, friction fit, threaded lock, toothed gear lock, snap fit lock, spring-actuated lock, or any other structure capable of securing the catheters and/or the control handles of the catheter.

For example, in FIG. 7A, outer sheath control handle 7120 (i.e., the exemplary sheath actuator) and guide catheter control handle 7140 (i.e., the exemplary guide actuator) may be mounted upon cradle 7180. Cradle 7180 may in turn be locked to stand 7400 and, in some embodiments, may be configured to be released from stand 7400 by actuation of release button 7184. In some embodiments, outer sheath control handle 7120 may be secured to cradle 7180 (for example, in a separable manner) such that relative longitudinal movement between handle 7120, cradle 7180, and by extension stand 7400 is prevented. In addition, and as discussed above, guide catheter control handle 7140 may include a toothed rack configured to engage a tooth gear of cradle 7180. The exemplary guide catheter control handle 7140 having a gear and rack mechanism may secure guide catheter control handle 7140 against longitudinal movement relative to cradle 7180 and stand 7400, unless knob 7188 is rotated. Moreover, implant catheter control handle 7160 may be secured against longitudinal movement relative to stand 7400 by slide lock 7166. Securing handles 7120, 7140, 7160 against longitudinal movement may, in turn, secure first catheter 7210, second catheter 7220, and third catheter 8100 against longitudinal movement since each catheter may be connected to, or otherwise secured relative to, its respective handle. As a result, the control handle assembly 7000, including stand 7400, may be configured to prevent relative longitudinal movement between, among other features, the first catheter 8400 and the second catheter 7220.

In some embodiments, the control handle assembly may be configured to steer the first catheter independently of adjustment of one or both of the first and second flexure radii. For example, the control handle assembly may include a first catheter steering mechanism configured to control bending of the first catheter. In some embodiments, the first catheter may include one or more bending portions configured for unidirectional bending or bidirectional bending. In some embodiments, the first catheter may include a bending portion within five centimeters of its distal end. For example, and without limitation, the first catheter may include a bending portion within five centimeters, four centimeters, three centimeters, two centimeters, or one centimeter of its distal end. The control handle assembly may include a first catheter steering mechanism (for example, within the capsule handle) configured to control bending of the one or more bending portions of the first catheter. In some embodiments, the first catheter steering mechanism may be actuated independently of the second catheter steering mechanism associated with the second catheter and the third catheter steering mechanism associated with the third catheter. Accordingly, a user may cause bending of the first catheter using the first catheter steering mechanism independently from the use of the second catheter steering mechanism and third catheter steering mechanism that control the first flexure radius and the second flexure radius, respectively. In the example illustrated in FIG. 7A, implant catheter control handle (i.e., the exemplary capsule handle) may include a steering knob 7168 configured to control bending of the implant catheter 8100 (i.e., the first catheter) at one or more bending portions thereof. Steering knob 7168 may thus be considered a first catheter steering mechanism. Although delivery system 7000 is depicted in FIG. 7A as including a knob 7168 to control bending of the first catheter, one of ordinary skill will understand that the exemplary delivery system may include any suitable mechanism for controlling catheter bending, such as a wheel, a slider, a lever, a joystick, a touchpad, a rotatable cuff, or any other structure configured to control catheter bending.

In some embodiments, one or both of the guide actuator and the sheath actuator may be connected to, or otherwise associated with, one or more pull wires connected to and configured to cause bending of the first flexure radius and the second flexure radius, respectively. For example, the second catheter may include one or more pull wires connected to a portion of the second catheter, and the third catheter may include one or more pull wires connected to a portion of the third catheter. For example, a pull wire may be connected to the distal end of the second catheter and/or of the third catheter. Additionally, or alternatively, one or more pull wires may be connected in proximity to one or both of the first and second flexure radii (e.g., distal to the flexure radius). According to such embodiments, the pull wires may be actuated to bend the first and second flexure radii. Alternatively, other suitable steering mechanisms may be incorporated within the exemplary delivery system to effect bending of one or both of the first and second flexure radii.

In some embodiments, the second flexure radius may be configured to remain substantially straightened while the first flexure radius is adjusted. In some embodiments, the bending portion of the second catheter can extend beyond the distal end of the third catheter, where bending of the bending portion of the second catheter (that is, the first flexure radius) does not cause bending of the bending portion of the third catheter (that is, the second flexure radius). The phrase "substantially straightened" may refer to a configuration of the third catheter in which the entire length of the third catheter, including flexure radii thereof, may be straight and unbent. For example, in FIGS. 7C and 7D, bending portion 7215 (i.e., the second flexure radius) may remain substantially straightened while bending portion 7225 (i.e., the first flexure radius) is adjusted because bending portion 7225 may be positioned outside of outer sheath 7210 (i.e., the exemplary first catheter).

In some embodiments, one or both of the first flexure radius and the second flexure radius may be configured to be adjusted by an angle greater than 90°, relative to straightened configurations thereof. The first flexure radius and the second flexure radius may be configured to be adjusted at different angles, each angle greater than 90°; additionally, or alternatively, the first flexure radius and the second flexure radius may be configured to be adjusted at the same angle greater than 90°. In some embodiments, the first flexure radius and the second flexure radius may each be configured to be adjusted by an angle up to and including 120°, relative to straightened configurations of the first flexure radius and the second flexure radius. In some embodiments, the adjustment of the first flexure radius and/or the second flexure radius may cause a resultant bend in the first catheter, since at least a portion of the first catheter may extend within the second and third catheters, including through the first and second flexure radii, respectively. In some embodiments, the first flexure radius and the second flexure radius may be configured to bend the first catheter by an angle greater than 180°, relative to a straightened configuration thereof. Put another way, the first and second flexure radii may be configured to bend the first catheter such that the distal end of the first catheter may form an angle equal to or greater than 180°, relative to the proximal end of the first catheter.

In some embodiments, the first catheter may be configured to advance the heart valve within a heart chamber while the second catheter and third catheter remain stationary relative to the heart chamber. For example, the first catheter may be configured to move longitudinally relative to the second and third catheters, which may remain stationary in their respective longitudinal positions. FIGS. 10A and 10B illustrate distal advancement of an exemplary heart valve within capsule 7300 through the atrium 9010 and into the ventricle 9020, while guide catheter 7220 (i.e., the exemplary second catheter) and outer sheath 7210 (i.e., the exemplary third catheter) remain stationary relative to the atrium 9010 and ventricle 9020. The prosthetic valve within capsule 7300 may be distally advanced by the implant catheter 8100 of FIGS. 7B and 8C (i.e., the exemplary first catheter), which is contained within capsule shaft 7230 (and thus, not visible in FIG. 10B). For example, advancement of the heart valve through the atrium and ventricle may be controlled by axial movement of implant catheter control handle 7160 of FIG. 7A, which may be connected to, or otherwise secured relative to, the implant catheter 8100. As illustrated in FIGS. 10C-10G, the heart valve may then be deployed within mitral valve 9030 via movement of proximal capsule portion 7320 and distal capsule portion 7340.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A heart valve delivery system, comprising:
   at least a first catheter, a second catheter, and a third catheter arranged in a telescoping configuration,
      wherein the first catheter is movable relative to the second catheter and the third catheter,
      wherein the first catheter extends from the distal end of the second catheter by a variable distance of between 0 and 20 centimeters, and
      wherein the second catheter is movable relative to the third catheter and extends from the distal end of the third catheter;
   a first adjustable flexure radius associated with the second catheter, the first flexure radius being located within five centimeters of the distal end of the second catheter, the first flexure radius configured to bend within a first steering plane;
   a second adjustable flexure radius associated with the third catheter, the second flexure radius configured to bend within a second steering plane, wherein the second flexure radius is configured to be adjusted within the second steering plane independently of adjustment of the first flexure radius within the first steering plane;
   a capsule secured to the first catheter,
      wherein a valve anchor is situated within the capsule, the valve anchor having a number of recesses configured to receive and retain a number of posts of a heart valve less than or equal to the number of recesses;
   an ejector associated with the capsule; and
   a control handle assembly configured to:
      permit at least two of the catheters to rotate together,
      independently adjust the first and second flexure radii within the first and second steering planes, respectively, while at least one of the second catheter or third catheter is secured against longitudinal movement,
      cause relative axial movement between the catheters, and
      permit the ejector to transmit a rotational movement to a longitudinal relative movement between the heart valve and the capsule, causing a ventricular side of the heart valve to be released from the capsule before an atrial side of the heart valve is released from the capsule.

2. The delivery system of claim 1, wherein the capsule includes an atrial capsule portion and a ventricular capsule portion, the atrial capsule portion and the ventricular capsule portion being configured for relative longitudinal movement.

3. The delivery system of claim 2,
   wherein the ventricular capsule portion is configured to retain an annular valve body of the heart valve and a plurality of ventricular anchoring legs of the heart valve therein, and
   wherein the atrial capsule portion is configured to retain a plurality of atrial anchoring arms of the heart valve therein.

4. The delivery system of claim 3, wherein the valve anchor is configured to engage the annular valve body of the heart valve, the ejector being configured to release the annular valve body from engagement with the valve anchor.

5. The delivery system of claim 4, wherein the ejector is further configured to effect movement between the capsule and the plurality of ventricular anchoring legs while the annular valve body remains engaged with the valve anchor.

6. The delivery system of claim 2, wherein an axial length of the ventricular capsule portion is at least twice as long as an axial length of the atrial capsule portion.

7. The delivery system of claim 2, wherein the control handle assembly is configured to assume:
- a capsule lock configuration in which the ejector is prevented from moving the ventricular capsule portion beyond a pre-determined location; and
- a capsule release configuration in which the ejector is permitted to move the ventricular capsule portion beyond the pre-determined location.

8. The delivery system of claim 1, wherein the ejector is situated at least partially within the first catheter.

9. The delivery system of claim 1, wherein the control handle assembly includes:
- a guide actuator configured to effect movement of the second catheter;
- a sheath actuator configured to effect movement of the third catheter; and
- a capsule handle configured to control the ejector,
- wherein the guide actuator, the sheath actuator, and the capsule handle are configured for relative longitudinal movement.

10. The delivery system of claim 9, wherein the capsule handle includes:
- a first release actuator configured to control relative movement between a first portion of the capsule and the heart valve, while the heart valve remains longitudinally fixed relative to the first catheter; and
- a second release actuator configured to control release of the heart valve from the capsule by the ejector.

11. The delivery system of claim 10, wherein the capsule handle is configured to assume:
- an anchoring configuration in which the second release actuator is prevented from controlling the ejector to release the heart valve from the capsule; and
- a final release configuration in which the second release actuator is permitted to control the ejector to release the heart valve from the capsule.

12. The delivery system of claim 11, wherein the second release actuator is configured to control relative movement between a second portion of the capsule and the heart valve while the capsule handle is in the anchoring configuration.

13. The delivery system of claim 9, wherein the capsule handle includes a slide lock configured to assume a locked position in which longitudinal movement of the first catheter is prevented, the capsule being configured for longitudinal movement relative to the first catheter when the slide lock is in the locked position.

14. The delivery system of claim 1, wherein the control handle assembly is further configured to prevent relative longitudinal movement between the first catheter and the second catheter.

15. The delivery system of claim 1, wherein the second flexure radius is configured to remain substantially straightened while the first flexure radius is adjusted.

16. The delivery system of claim 1, wherein the first flexure radius and the second flexure radius are each configured to be adjusted by an angle greater than 90°.

17. The delivery system of claim 16, wherein the first flexure radius and the second flexure radius are each configured to be adjusted by 120°.

18. The delivery system of claim 1, wherein the first flexure radius and the second flexure radius are configured to bend the first catheter by an angle greater than 180°.

19. The delivery system of claim 1, wherein the first catheter is configured to advance the heart valve within a heart chamber while the second catheter and third catheter remain stationary relative to the heart chamber.

20. The delivery system of claim 1, wherein the first steering plane is angled relative to the second steering plane.

21. The delivery system of claim 1, wherein the control handle assembly is configured to independently adjust the first and second flexure radii within the first and second steering planes, respectively, while both of the second catheter and third catheter are secured against longitudinal movement.

* * * * *